United States Patent
West et al.

(10) Patent No.: US 10,799,145 B2
(45) Date of Patent: Oct. 13, 2020

(54) METHOD AND SYSTEM TO FACILITATE INTRAOPERATIVE POSITIONING AND GUIDANCE

(71) Applicant: THE CLEVELAND CLINIC FOUNDATION, Cleveland, OH (US)

(72) Inventors: Karl West, Cleveland, OH (US); Vikash Goel, Cleveland, OH (US); James Foster, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 500 days.

(21) Appl. No.: 14/209,300

(22) Filed: Mar. 13, 2014

(65) Prior Publication Data
US 2014/0276002 A1 Sep. 18, 2014

Related U.S. Application Data

(60) Provisional application No. 61/914,700, filed on Dec. 11, 2013, provisional application No. 61/787,762, filed on Mar. 15, 2013.

(51) Int. Cl.
*A61B 5/06* (2006.01)
*G06T 19/00* (2011.01)
(Continued)

(52) U.S. Cl.
CPC .............. *A61B 5/061* (2013.01); *A61B 34/20* (2016.02); *G06T 19/00* (2013.01); *A61B 90/361* (2016.02);
(Continued)

(58) Field of Classification Search
None
See application file for complete search history.

(56) References Cited

U.S. PATENT DOCUMENTS

| 6,533,455 B2 | 3/2003 | Graumann et al. |
| 7,010,095 B2 | 3/2006 | Mitschke et al. |

(Continued)

FOREIGN PATENT DOCUMENTS

| EP | 1421913 A1 | 5/2004 |
| JP | 2007185278 A | 7/2007 |

(Continued)

OTHER PUBLICATIONS

International Search Report and Written Opinion for PCT/US2014/026174, dated Aug. 5, 2014, pp. 1-14.

(Continued)

*Primary Examiner* — Oommen Jacob
*Assistant Examiner* — Shahdeep Mohammed
(74) *Attorney, Agent, or Firm* — Tarolli, Sundheim, Covell & Tummino LLP

(57) ABSTRACT

System and methods are disclosed to facilitate intra-operative procedures and planning. A method can include storing tracking data in memory, the tracking data being generated by a tracking system to represent a location of an object in a tracking coordinate system of the tracking system. The method can also include storing a patient-specific implicit model in memory, the patient-specific implicit model being generated based on image data acquired for the patient to define geometry of an anatomical structure of the patient. The method can also include registering the tracking data and the patient-specific implicit model in a common three-dimensional coordinate system. The method can also include generating an output visualization representing a location of the object relative to the geometry of the anatomical structure of the patient in the common coordinate system.

28 Claims, 14 Drawing Sheets

(51) Int. Cl.
*A61B 34/20* (2016.01)
*A61B 34/10* (2016.01)
*A61B 90/00* (2016.01)

(52) U.S. Cl.
CPC . *A61B 2034/105* (2016.02); *A61B 2034/2051* (2016.02); *A61B 2090/363* (2016.02); *A61B 2090/364* (2016.02); *A61B 2090/376* (2016.02); *A61B 2090/3762* (2016.02); *A61B 2090/3966* (2016.02); *A61B 2090/3983* (2016.02); *G06T 2210/41* (2013.01)

(56) References Cited

U.S. PATENT DOCUMENTS

| | | | |
|---|---|---|---|
| 7,556,428 B2 | 7/2009 | Sukovic et al. | |
| 7,671,887 B2 | 3/2010 | Pescatore et al. | |
| 7,824,328 B2 | 11/2010 | Gattani et al. | |
| 8,060,185 B2 | 11/2011 | Hunter et al. | |
| 8,213,693 B1* | 7/2012 | Li | A61B 34/20 382/128 |
| 8,219,179 B2 | 7/2012 | Ganatra et al. | |
| 8,224,632 B2 | 7/2012 | Whirley et al. | |
| 8,238,625 B2 | 8/2012 | Strommer et al. | |
| 8,248,413 B2 | 8/2012 | Gattani et al. | |
| 8,301,226 B2 | 10/2012 | Csavoy et al. | |
| 8,315,355 B2 | 11/2012 | Mohamed | |
| 8,467,853 B2 | 6/2013 | Hunter et al. | |
| 2003/0011624 A1 | 1/2003 | Ellis | |
| 2007/0055128 A1* | 3/2007 | Glossop | A61B 1/005 600/407 |
| 2008/0020362 A1 | 1/2008 | Cotin et al. | |
| 2009/0227861 A1 | 9/2009 | Ganatra et al. | |
| 2010/0210938 A1* | 8/2010 | Verard | A61B 1/00071 600/424 |
| 2010/0312094 A1 | 12/2010 | Guttman et al. | |
| 2011/0026793 A1* | 2/2011 | Goel | G06T 7/60 382/131 |
| 2011/0054300 A1 | 3/2011 | Yamamoto et al. | |
| 2011/0166446 A1 | 7/2011 | Whitmore, III et al. | |
| 2011/0295109 A1 | 12/2011 | Lavallee et al. | |
| 2013/0079628 A1* | 3/2013 | Groszmann | A61B 6/12 600/424 |

FOREIGN PATENT DOCUMENTS

| | | |
|---|---|---|
| JP | 2007209531 A | 8/2007 |
| JP | 2008061858 A | 3/2008 |
| JP | 2008136850 A | 6/2008 |
| JP | 2009072317 A | 4/2009 |
| JP | 2012147858 A | 8/2012 |
| JP | 2012529352 A | 11/2012 |
| WO | 2005119578 A2 | 12/2005 |
| WO | 2008/035271 A2 | 3/2008 |
| WO | 2010/074986 A1 | 7/2010 |
| WO | 2010086374 A1 | 8/2010 |
| WO | 2012127353 A1 | 9/2012 |
| WO | 2012143290 A1 | 10/2012 |

OTHER PUBLICATIONS

Mohapatra et al., "Raditaion Exposure to Operating Room Personnel and Patients During Endovascular Procedures", Journal of Vascular Surgery, 2013, pp. 1-8.

JP Office Action for Application No. 2016-502070, forwarded dated Sep. 13, 2016, pp. 1-2.

Canadian Office Action dated Oct. 31, 2016 for corresponding PCT/US2014/026174, pp. 1-4.

JP Office Action for Application No. 2016-502070, dated Sep. 13, 2016, pp. 1-2.

European Exam Report for corresponding European Patent Application No. 14 721 077.7, dated Mar. 13, 2018, pp. 1-5.

Japanese Office Action for corresponding Japanese Application Serial No. 2017-173862, dated Aug. 1, 2018, pp. 1-8.

Japanese Office Action for corresponding Japanese Application Serial No. 2017-173862, dated May 28, 2019, pp. 1-4.

\* cited by examiner

METHOD AND SYSTEM TO FACILITATE INTRAOPERATIVE POSITIONING AND GUIDANCE

CROSS-REFERENCE TO RELATED APPLICATION

This application claims the benefit of U.S. Provisional Patent Application No. 61/787,762, filed Mar. 15, 2013 and entitled INTRA-OPERATIVE POSITIONING SYSTEM, and also claims the benefit of U.S. Provisional Patent Application No. 61/914,700, filed Dec. 11, 2013, 2013 and entitled SYSTEM AND METHOD TO FACILITATE INTRAOPERATIVE POSITIONING AND GUIDANCE, each of which applications is incorporated herein in its entirety.

TECHNICAL FIELD

This disclosure relates to a method and system to facilitate intraoperative positioning and guidance.

BACKGROUND

Low invasive techniques for accessing various body parts has become common practice for diagnostic purposes, therapeutic purposes and other surgical purposes. For example, health care providers can percutaneously access the gastrointestinal tract, respiratory tract, urinary tract and vasculature. In some cases, the objects being inserted into the patient may be directly visible, but in other situations no direct line of sight may exist.

For the example of endovascular surgery or other procedures where no direct line of sight exists, x-ray fluoroscopy is often utilized to obtain images to assist introduction and guidance of objects through patient anatomy. The increased use of x-ray c-arm fluoroscopy for guiding endovascular and other devices has resulted in escalating concerns on the risks of radiation exposure to patients and operating room staff.

SUMMARY

This disclosure relates to a method and system to facilitate intraoperative positioning and guidance.

As one example, a method can include storing tracking data in memory, the tracking data being generated by a tracking system to represent a location of an object in a tracking coordinate system of the tracking system. The method can include storing a patient-specific implicit model in memory, the patient-specific implicit model being generated based on image data acquired for the patient to define geometry of an anatomical structure of the patient. The method can also include registering the tracking data and the patient-specific implicit model in a common three-dimensional coordinate system. The method can also include generating an output visualization representing a location of the object relative to the geometry of the anatomical structure of the patient in the common coordinate system.

As another example, a system can include memory to store tracking data, the tracking data being generated by a tracking system to represent a location of an object in a tracking coordinate system. Memory can also store a patient-specific implicit model to define geometry of patient anatomy of a given patient in an image coordinate system. A registration engine can be programmed to compute a registration matrix based on the tracking data and image data. The registration engine can be programmed to apply the registration matrix to the tracking data to transform the tracking data from a coordinate system of the tracking system to the image coordinate system. An output generator can generate a graphical visualization representing a location of the object relative to the geometry of the patient anatomy in the image coordinate system.

DETAILED DESCRIPTION

This disclosure relates to a method and system to facilitate intraoperative positioning and guidance of an object.

The approach disclosed herein receives and stores tracking data in memory. The tracking data can represent a location of an object that is being moved within an anatomical structure (e.g., a tubular structure) of a patient's body. The tracking data can represent a location of the object without the use of ionizing radiation. For example, one or more sensors can be coupled to the object being tracked and provide sensing signals in response to a field provided by a tracking system. The tracking system can determine the tracking data to indicate a three-dimensional position and orientation of the object in a coordinate system of the tracking system. The tracking data can be registered into a three-dimensional coordinate system in which a patient-specific implicit model is also registered. The patient-specific implicit model can be generated based on image data acquired for the patient to define geometry of the anatomical structure of the patient. The image data used to generate the patient-specific implicit model can be acquired before the intraoperative procedure that is being tracked by the tracking system. For example, the image data can be acquired as part of a preoperative planning stage.

An output visualization can be generated based on the registered tracking data and the implicit model to render a corresponding three-dimensional graphical representation of the object at a position relative to the anatomical structure of the patient. For example, the position, direction and shape of the object can be tracked, represented and visualized in an intuitive 3D shaded surface model of the patient's anatomy. The implicit model of the patient anatomy enables the visualization to be rendered and updated such as to provide a substantially real time dynamic visualization of the intraoperative procedure in the absence of any direct line of sight. Moreover, the approach can eliminate or at least significantly reduce ionizing radiation that is typically used intraoperatively during many procedures.

Figure 1:
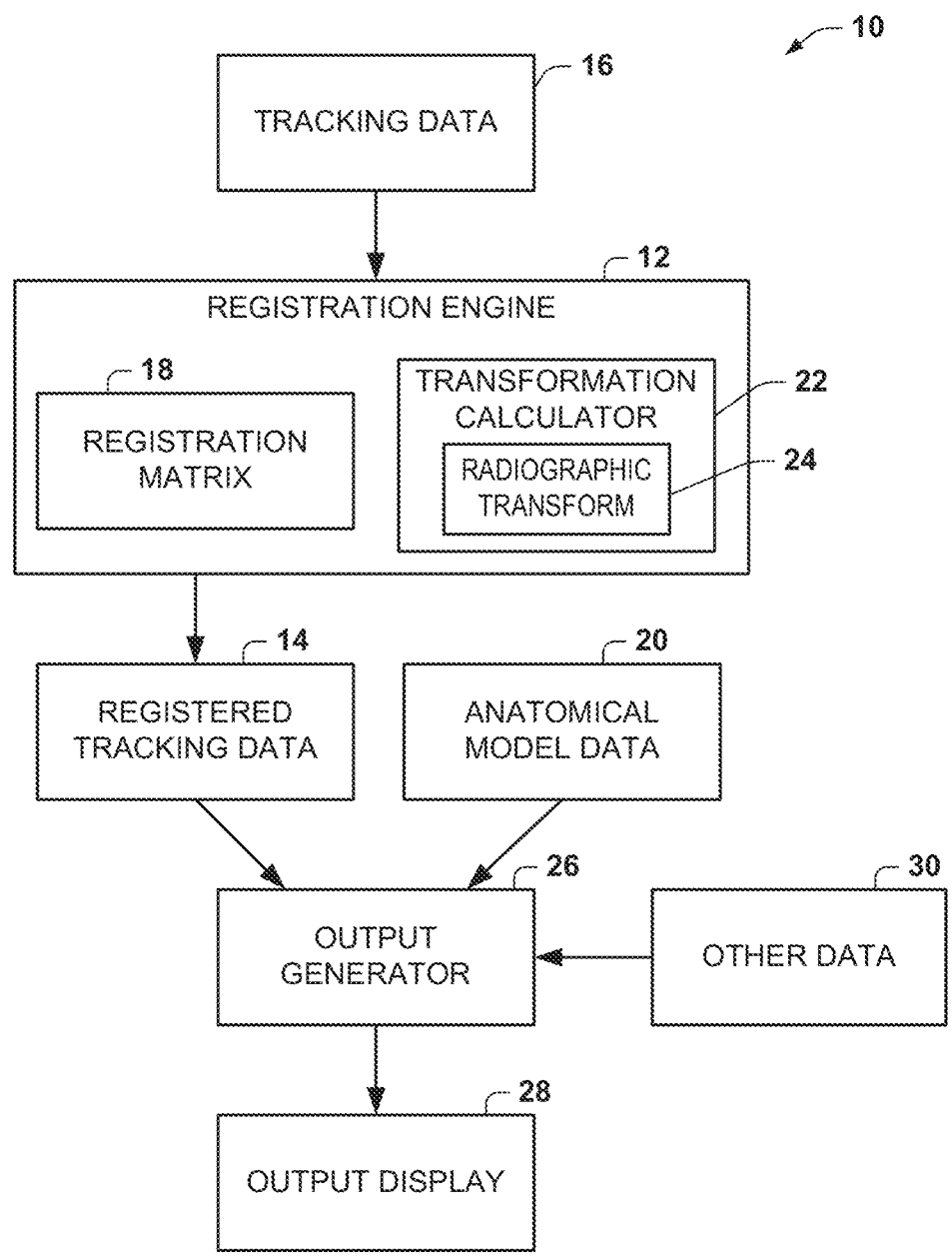
FIG. 1 depicts an example of an intraoperative positioning system.

FIG. 1 depicts an example of a system 10 to facilitate intraoperative guidance and positioning. The system 10 includes a registration engine 12 that is configured to compute registered tracking data 14 based on input tracking data 16. The input tracking data 16 can be provided by a tracking system, such as in response to non-ionizing radiation that is provided to a patient to track the position of one or more sensors that can be integrated into an object, such as an instrument or an implantable device. As used herein, non-ionizing radiation can refer to any type of electromagnetic radiation that does not carry enough energy per quantum to ionize atoms or molecules—that is, to completely remove an electron from an atom or molecule. Instead of producing charged ions when passing through matter, the electromagnetic radiation provided by the tracking system can have sufficient energy only for excitation, the movement of an electron to a higher energy state. Other types of tracking systems, such as ultrasonic sensors or the like, can also be employed to provide the tracking data. The tracking data 16 can include a position and orientation (e.g., a vector) for each sensor that can be detected by the tracking system.

The registration engine 12 is programmed to compute a registration matrix 18 that can convert the tracking data 16 from a coordinate system of the tracking system into a coordinate system that is common to anatomical model data 20. For example, the anatomical model data 20 can represent geometry for one or more anatomical structure of a patient by an implicit model. As used herein, an implicit model can represent a geometric structure by a small number of parameters. For example, the implicit model data 20 can represent parameters that define the geometry of a physical anatomical structure of a patient that can be generated based on imaging data. In the example of a tubular anatomical structure, the implicit model can include parameters that define the geometry of a centerline and surface of the tubular anatomical structure. As an example, the implicit model can be implemented as a lofted basis (b-) spline.

The imaging data used to generate the implicit model can be acquired by an imaging modality, such as computed tomography (CT), magnetic residence imaging, multi-plane x-ray or the like, which can be configured to provide a three-dimensional image of patient anatomy in a coordinate system of the imaging modality. Since the tracking data 16 is generated in a coordinate system of a tracking system that is different from the anatomical model data 20, the registration engine 12 can be configured to convert the tracking data into the coordinate system in which the anatomical model data resides or another common coordinate system.

As an example, the anatomical model can be generated based on preoperative imaging data whereas the tracking data 16 can be generated by the tracking system intraoperatively such as to provide real time tracking data corresponding to a position and orientation of each sensor that is monitored by the tracking system. For example, each of the one or more sensors can be attached to an object that is moveable relative to the patient. For example, a sensor detectable by the tracking system can be attached to a guide wire, a catheter, a stent, or other device that may be transluminally moved and positioned within the patient's body. In some examples, each sensor can be detectable by the tracking system to enable tracking in five or six degrees of freedom. Examples of sensors that can be detected by an electromagnetic type of tracking system are commercially available from Northern Digital, Inc., of Ontario, Canada. Other types of sensors can be used depending on the type of tracking system.

The registration engine 12 can include a transformation calculator 22 that is programmed to compute a transform to which the tracking data can be applied for generating a corresponding registration matrix 18. For example, the transformation calculator 22 can employ a radiographic transform 24, such as can be generated based upon the imaging data that is utilized to construct the anatomical model data 20 and the intraoperative imaging data corresponding to the position of the patient during a procedure. The radiographic transform 24 thus can be a fixed transform that can be applied to one or more frames to which the tracking data 16 is captured over time. The transformation calculator 22 can accommodate movement of the patient and/or sensors being monitored by the tracking system. For example, the registration matrix 18 can recompute the registration matrix to provide a corresponding transformation for each frame of tracking data to convert the position and orientation of a predetermined location on the object being tracked (e.g., at each sensor location) into the registered tracking data 14 that is in the same coordinate system as the anatomical model 20. As disclosed herein, the registered tracking data 14 can represent position and orientation for any number of one or more objects in such common coordinate system.

An output generator 26 can be configured to generate a graphical visualization based on the registered tracking data and the anatomical model data. The graphical visualization can be provided to an output display 28 for viewing by one or more users. The output generator 26 further can be programmed to render a graphical visualization of the anatomical structure that is represented by the anatomical model data 20. The one or more points in orientation of the object represented by the registered tracking data can also be rendered in the graphical visualization that is generated.

The output generator 26 can also render graphical representation of an object to which the sensor is associated. For example, the sensor can be attached to a catheter or guide wire having one or more parts that can be movable relative to the patient. By attaching the sensor to a predetermined location of such object, the registered tracking data 14 can correspond to an identifiable point for the object that can provide an origin for graphically rendering a representation of the object in the output visualization superimposed in conjunction with a rendering of the anatomical structure.

As a further example, the output generator 26 can employ other data 30 in generating the output visualization. The other data 30 can represent a model or other representation form that can drive rendering based on the registered tracking data 14. The other data 30 can be stored in memory and accessed by the output generator 26 according to a specification of the object to which the sensor is attached. This can be set in response to a user input or can be determined automatically based on data acquired by the system 10 or otherwise. For example, the other data 30 can include a library of objects (e.g., instruments and/or implantable devices) that can be selectively used. Each object in the library can include a respective model for rendering the object and location of one or more sensors attached at a predetermined location to the object. Such a library of models thus can be constructed for each of the different types and available devices that are being utilized in the system 10. The modeling of each object further can correspond to an implicit object model, such that small number of parameters can define the entire geometry of the corresponding device structure as well as its behavior characteristics.

By way of further example, the other data 30 can represent the geometry and behavioral characteristics and a variety of devices. For instance, such geometry and behavioral characteristics can be derived based on CAD modeling that may be provided by a manufacturer of an instrument or implantable device or be determined based upon structural analysis of a given device.

Figure 2:
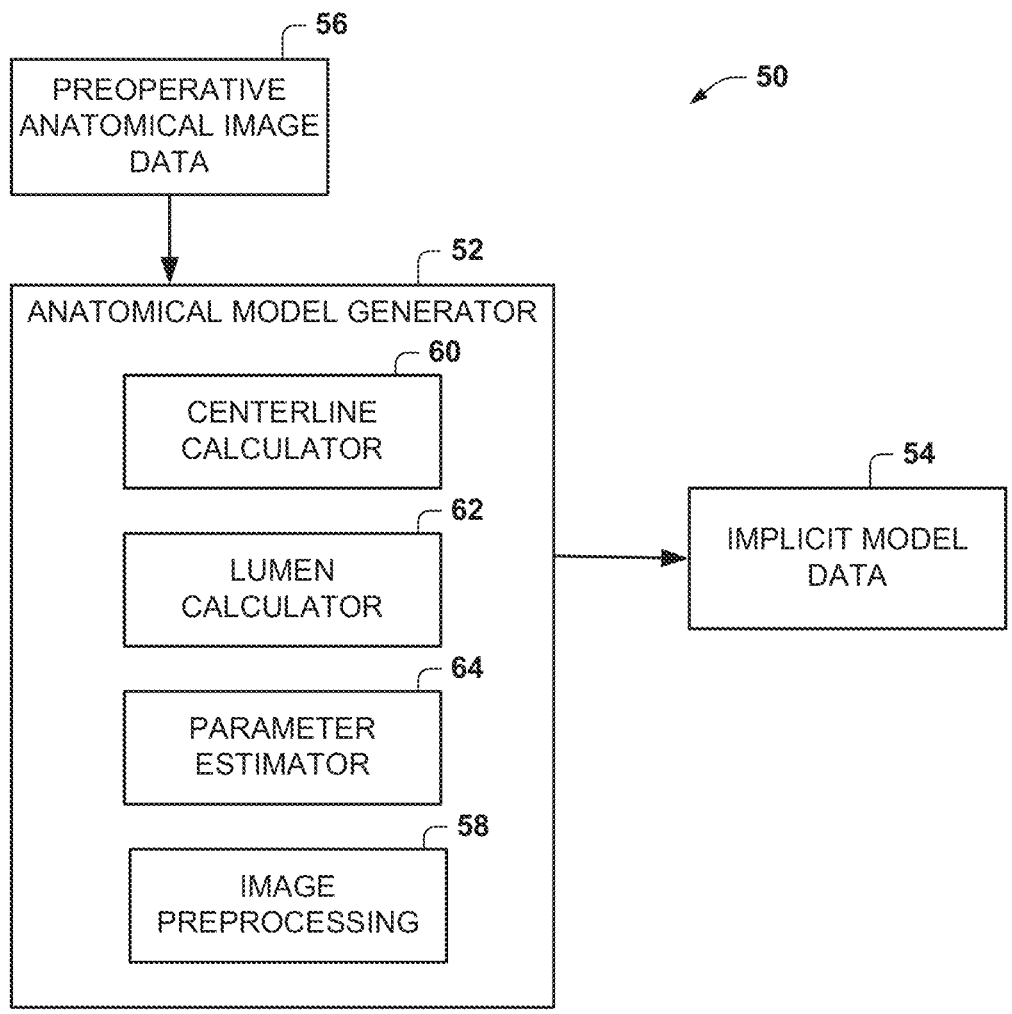
FIG. 2 depicts an example of a subsystem that can be utilized to generate an implicit model.

FIG. 2 depicts an example of a system 50 that can be utilized for generating an implicit model such as for a tubular anatomical structure. The system 50 includes an anatomical model generator 52 that is programmed to generate an implicit model data 54 based on anatomical image data 56. The anatomical image data 56, for example, can be acquired by preoperatively for a given patient by an image modality. As an example, the preoperative image data 56 can correspond to a preoperative arterial CT scan for a region of interest of the patient, such as can be acquired weeks or months prior to a corresponding operation. Other imaging modalities can be used to provide three dimensional image data 56, such as MRI, ultrasonography, positron emission tomography or the like. Such scans are common part of preoperative planning in a surgical workflow to help size prostheses and to plan surgery or other interventions.

The corresponding image data 56 can be stored in memory that can be accessed by or transferred to an intraoperative positioning system (e.g., the system 10 of FIG. 1). The image data 56 can include image data representing pixels (two-dimensional slices) or voxels (three-dimensional image information) corresponding to patient anatomy. The image data 56 can also include one or more transformations that can specify a translation of the pixels or voxels from an image space to a corresponding three-dimensional coordinate system. Such transformation can be provided as metadata, for example, as part of the image data 56. Thus the preoperative image data 56 contains information sufficient to convert coordinates of points (pixels) or volumes (voxels) of image data in the image space to the corresponding three-dimensional coordinate system corresponding to the imaging modality.

The anatomical model generator 52 is programmed to generate the implicit model data 54 based on processing the input image data 56. As an example, the anatomical model generator 52 can implement image pre-processing 58. The image preprocessing can include automated and/or manual processes, such as to perform background correction, segmentation and thresholding for identification of a corresponding anatomic structure of interest. For example, the anatomical structure can correspond to a major blood vessel as well as one or more branches that may extend from such vessel. For instance, the vessel can correspond to a patient's descending aorta and associated renal arteries as well as other branches thereof. In other examples, the anatomical structure can correspond to an intestinal tract, a portion of a respiratory tract, the patient's digestive tract or other anatomical structures in which objects may be positioned transluminally for a variety of diagnostic and surgical purposes.

The model generator 52 can also include a centerline calculator 60. The centerline calculator can be programmed to compute a corresponding centerline for the elongated tubular anatomical structure. As one example, the centerline can be computed as a pixel or voxel thickness extending longitudinally along the central axis of the structure. A corresponding surface boundary of the tubular structure can be computed by a lumen calculator 62. The tubular structure can correspond to a surface of the anatomical structure having a corresponding functional relationship relative to the centerline along the length of the structure as computed by the centerline calculator 60.

A parameter estimator 64 can compute a set of model parameters corresponding to the centerline and surface of the lumen structure, which parameter can correspond to the implicit model data 54. The set of parameters can be a small set of parameters such as corresponding to a lofted b-spline (basis spline) function for the elongated anatomical structure. As one example, the anatomical model generator 52 can be programmed to compute the implicit model data according to the disclosure of U.S. Patent Publication No. 2011/0026793 entitled Automated Centerline Extraction Method and Generation of Corresponding Analytical Expression and Use Thereof, which is incorporated herein by reference. Another example of generating an implicit model for tubular anatomical structures is disclosed in *Analytical centerline extraction and surface fitting using CT scans for aortic aneurysm repair*, Goel, Vikash R, Master's Thesis, Cornell University (2005), which is incorporated herein by reference. Other approaches for generating the implicit model data can also be utilized. Other types of geometric representations can also be utilized to provide the implicit model data 54. For example, parameters representing lofted ellipses or triangular meshes can be generated to provide the anatomical model data 54 representing the patient's anatomical structure of interest.

Figure 3:
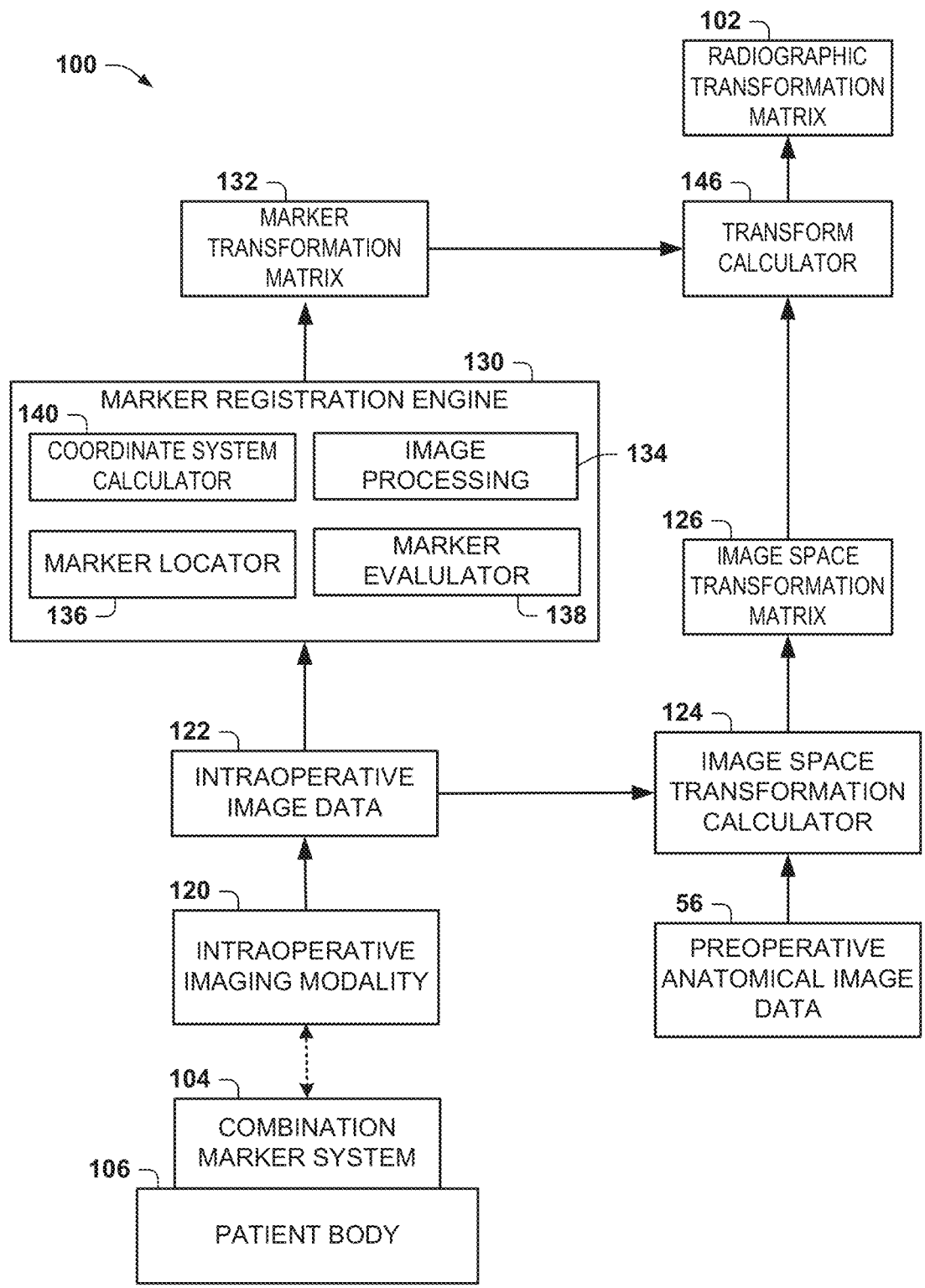
FIG. 3 depicts an example of a subsystem that can be utilized to generate a transformation matrix.

FIG. 3 depicts an example of a subsystem 100 that can be utilized for generating a radiographic transformation matrix 102. The radiographic transformation matrix 102 can provide a transformation from a preoperative coordinate system to a corresponding coordinate system of a combination marker system 104 that can be attached to a patient's body 106. The combination marker system 104 can include a plurality of radio opaque objects, such as fiduciary markers, arranged in a pre determined relationship relative to each other. As used herein, radio opaque refers to the inability of ionizing electromagnetic radiation to pass through sufficient to make the objects visible in a corresponding image obtained by an imaging modality 120. Thus, the radio opaque objects can be radiodense materials with respect to the imaging modality 120.

The combination marker system 104 can also include one or more sensors having a predetermined position relative to the radio opaque fiduciary markers. The combination marker system can include any number of one or more combination markers that may be attached to a patient's body, such as to a patient's torso (e.g., to a patient's back) at a location that is close to the anatomical structure of interest. By way of example, the marker system 104 can include two or more (e.g., three) markers that can be placed to the region of tracking interest. In some examples, the marker system 104 can include a plurality of spaced apart combination markers. For an example of a procedure in which an endovascular device is to be positioned or tracked within a descending aorta, the tracking system can be placed close to where the renal artery is attached to the aorta. Other locations could be utilized depending upon the region of tracking interest.

Figure 4:
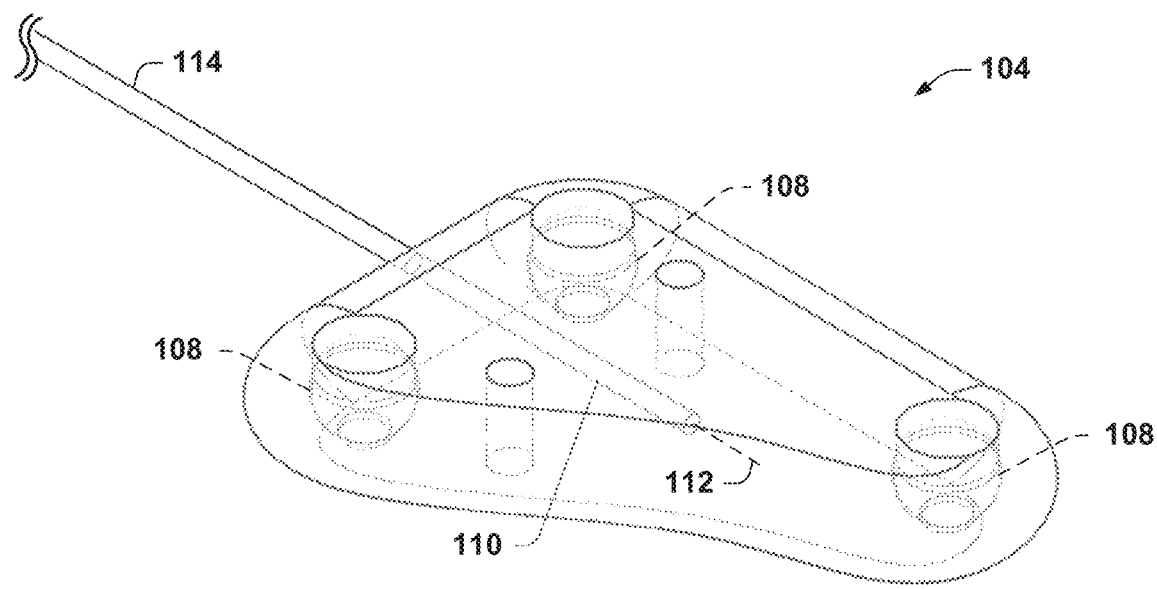
FIG. 4 depicts an example of a combination marker.
Figure 5:
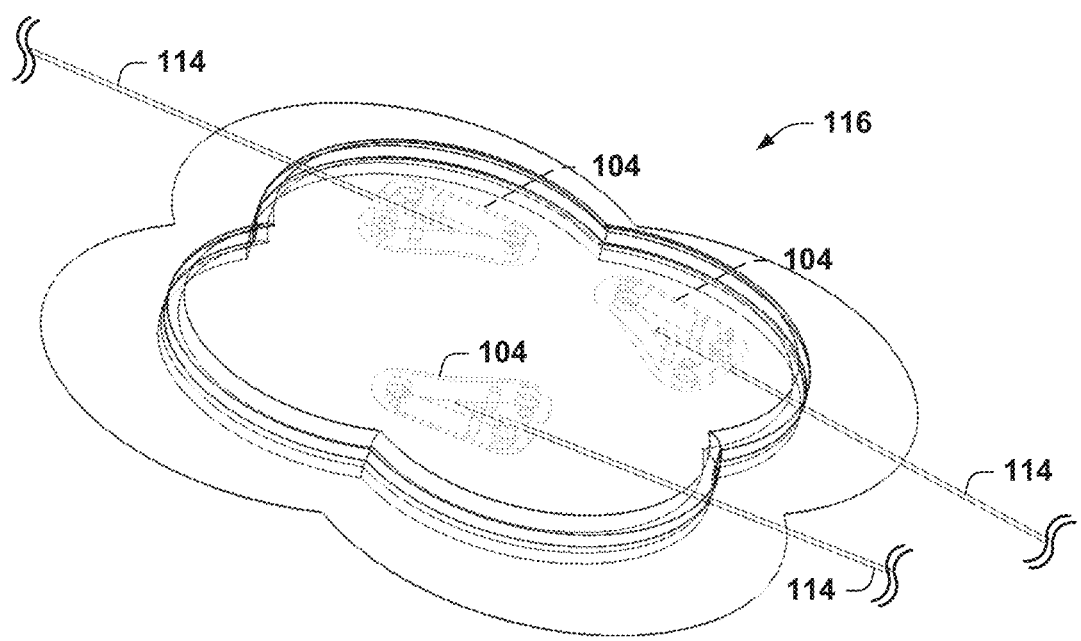
FIG. 5 depicts an example of a plurality of combination markers implemented in a structure configured for attachment to a patient.

An example of a combination marker system 104 is demonstrated in the examples of FIGS. 4 and 5. In FIG. 4, a single combination marker system 104 is demonstrated. In this example, the combination marker system 104 includes a plurality of radio opaque fiduciary structures 108 having a predetermined geometry and a range with a predetermined geometric relationship relative to each other. For example, the radio opaque objects 108 can be implemented as spheres such as having a predetermined angular orientation and spatial arrangement (e.g., configured as a scalene right triangle). Thus, each of the radio opaque objects 108 can be identified in a corresponding radiograph (e.g., obtained intraprocedurally via a CT scan, bi-plane x-ray or the like). As mentioned, the type of material utilized for the respective objects 108 can vary depending upon the imaging modality 120 being utilized. The combination marker 104 also includes one or more sensors 110 detectable by the tracking system. Each sensor 110 can be dimensioned and configured to have a predetermined spatial relationship (e.g., distance and angle) relative to the geometry of the respective radio opaque objects 108. For example, the sensor 110 can include an elongated sensor that is positioned at the origin of a pair of axes that can be computed based on the geometric relationship of the objects 108. Additionally, the sensor itself 110 can extend along an axis 112 or be parallel to an axis defined by the respective radio opaque objects 108.

Figure 6:
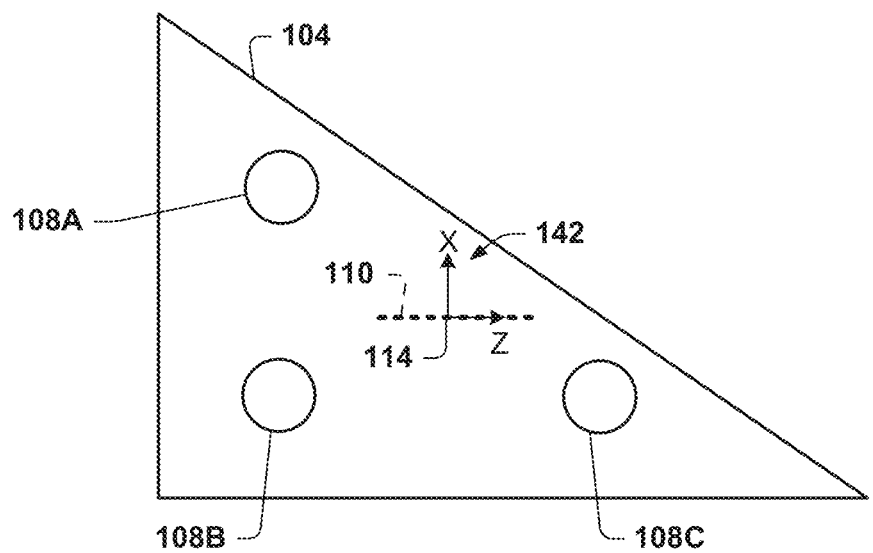
FIG. 6 depicts an example of geometry associated with a combination marker.

FIG. 6 demonstrates example geometry for a corresponding coordinate system 142 that can be determined for the combination marker 104 (FIG. 4). In the example of FIG. 6, the coordinate system 142 includes X and Z axis lying in the plane of the triangle (of the page) with the corresponding Y axis extending perpendicular to the plane (e.g., the page in which the figure is demonstrated). As demonstrated in FIG. 6, a sensor body 110' is shown to extend along the Z axis of the coordinate system 142. A center of a body of the sensor 110, demonstrated at 114, is at the origin of the X, Y, and Z axes. As disclosed herein, the sensor 110 can be configured as an elongated coil that extends axially along a length of the Z axis, and is detectable by the tracking system. For example, the sensor 110 can be implemented as a coil of the electrically conductive material within the combination marker system 104 with a center of the sensor coil located an origin of a corresponding coordinate system 142.

FIG. 5 demonstrates a marker pad device 116 that can help protect the patient's skin from the hard surface of the combination markers. One or more of the combination marker systems 104 (FIG. 4) can be implemented within the pad device 116 to enable co-registration between the domain of the tracking system and domain of the intraoperative image data, such as disclosed with respect to FIG. 3. For example, the pad 116 can contain a gel or other soft flexible material to provide a cushion around each combination marker.

In the example of FIG. 5, the pad device 116 includes three combination markers 104 distributed in a spaced apart arrangement with respect to each other. The pad device 116 can be configured to hold each of the combination markers in a substantially fixed spatial relationship while allowing flexibility to accommodate patient movement. Each of the combination markers 104 also includes a corresponding connection 115 that can be connected to the tracking system. For example, the tracking system can be implemented as an electromagnetic tracking system, such as disclosed herein, and each of the connections 115 thus can provide an electrical signal to the tracking system representing induced current in response to an electromagnetic field that is generated by a transmitter of the tracking system and detected by the respective sensing coil. In other examples, the connections can be wireless and the sensors can communicate via RF or other wireless technology. The tracking system can convert the sensor signals into corresponding tracking system data, which can be analyzed as disclosed herein. For example, the tracking data can include a position and orientation of a point in a three-dimensional coordinate space with respect to the transmitter of the tracking system for each combination marker 104.

Returning to FIG. 3, an intraoperative imaging modality 120 can be utilized to generate intraoperative image data 122 corresponding to the patient geometry for at least the region of tracking interest in the patient's body as well as the combination marker system 104 that has been attached to the patient's body. As mentioned above, the system 100 can also utilize the preoperative anatomical image data 56, which can be obtained using the same or a different type of imaging modality that is utilized for the intraoperative imaging modality 120.

An image space transformation calculator 124 can be configured to register the intraoperative image data 122 to a corresponding coordinate system of the preoperative image data 56. The computation by the transformation calculator 124 can be facilitated based on transform metadata provided by the imaging modality for converting the image pixels or voxels to points or volumes within a coordinate system of the imaging modality 120. The image space transformation calculator 124 thus can generate a corresponding image space transformation matrix 126 that provides a transformation of the intraoperative image data 122 into the preoperative image data 56 (FIG. 2). The image space transformation matrix 126 can also be utilized to enable the markings or other information from a preoperative scan to be overlaid on corresponding intraoperative fluoroscopy images obtained during a corresponding procedure. The intraoperative image data 122 and the preoperative image data 56 can be stored in memory such as in one or more non-transitory computer readable media. In some examples the memory can be accessible via a network or the memory can be a portable storage device such as a solid state memory device (e.g., flash drive or the like).

The subsystem 100 also includes a marker registration engine 130 programmed to generate an image-marker transformation matrix 132 based on the intraoperative imaging data 122. The image-marker transformation matrix encodes the location of the combination marker system 104 (or at least a portion thereof) along with an orientation of the marker provided therein based on the intraoperative image data 122. The marker registration engine 130 can include an image processing component 134 that is programmed to process the intraoperative image data 122 for identifying the radio opaque fiduciary markers (e.g., markers 108 of FIGS. 4 and 5). The image preprocessing 134 can include thresholding and image segmentation to produce an edge detected data set of pixels and/or voxels representing boundaries of each radio opaque fiduciary marker 108.

A marker locator 136 can compute a corresponding distance transformation of the edge detected data set. As an example, the marker locator 136 can compute a distance for each pixel or voxel in the image data 122 relative to the edge detected data set. For instance, a partial transformation can be utilized such that the computations only compute the distance for voxels at the edge or within the boundary of each fiduciary marker. A corresponding computed distance value can be stored for each voxel. For example, the distance transformation can provide a voxel set that contains for each respective voxel a distance to a nearest edge of the radio opaque fiduciary marker such as can correspond to a sphere. The marker locator 136 can analyze the distance transform data set along a corresponding axis (e.g., extending from feet to head or anterior to posterior or left to right for the presence of a sphere at each respective location.

A marker evaluator can be programmed to evaluate whether a particular location in a voxel data set is the center of a sphere such as by calculating a surface integral of the distance transformation over the surface of a respective sphere in such center. If the sphere is determined to be present for the voxels being evaluated, the surface interval should approximate zero. Accordingly, a threshold can be set (e.g., a tunable threshold) to compare relative to the surface integral to identify whether or not the location should be recorded as a sphere. The marker evaluator thus can test all potential locations for radio opaque markers and compare the points to ascertain the marker does in fact exist at such location. Each cluster having a value that is below the tunable threshold can be identified as a radio opaque marker and a mean of such locations can in turn be utilized for identifying a corresponding radio opaque marker.

With reference back to FIG. 6, after all such spheres have been identified based on intraoperative image data, each possible grouping of the radio-opaque markers 108 can be evaluated to locate each composite marker. For example, the distances between each of the respective markers 108 (distance between centroids thereof) can be tested to determine if the distances match the predetermined lengths of legs for the triangle formed by the radio opaque markers in the physical design of the combination marker. In the example of FIG. 6, each of the markers 108 is identified as markers 108*a*, 108*b*, and 108*c*.

In the example of FIG. 3, the marker registration engine 130 includes a transformation matrix calculator 140. The transformation matrix calculator 140 is programmed to compute a coordinate system 142 for each combination marker. For example, an origin 114 of the coordinate system can reside at a centroid of a triangle formed between markers 108*a*, 108*b* and 108*c*. As mentioned above, a center of the sensor (detectable by the tracking system) 110 can be located at the origin of the coordinate system 142 or have another predetermined spatial relationship with respect to the markers 108*a*, 108*b* and 108*c*.

The transformation matrix calculator 140 can also be programmed to compute the corresponding image-marker transformation matrix 132. The transformation matrix calculator 140 can compute the transformation matrix 132 as a translation component to encode the location of the centroid of the triangle and include a rotation component that encodes the orientation of the respective marker 104. The rotation can correspond to a change of basis function, for example. For the coordinate system 144, an X basis vector can represent the normalized vector for the sphere by to the marker 108*a*. The Z basis vector can correspond to the normalized vector marker extending from 108*b* to marker 108*c*. The Y basis vector can correspond to the process product of the Z and X basis vectors. After the transformation matrix calculator 140 computes the Y vector, each of the respective X and Z vectors can be adjusted, if necessary, to ensure that all vectors are mutually orthogonal. The output of the corresponding coordinate system can be provided as the image-marker transformation matrix 132.

The system 100 further includes a transform calculator 146 that is programmed to generate the radiographic transformation matrix 102 based on the image-marker transformation matrix 132 and the image space transformation matrix 126. The transform calculator 146, for example, can compute the radiographic transformation matrix by concatenating the image-marker transformation matrix 132 with an inverse of the image space transformation matrix 126. As a result, the radiographic transformation matrix 102 can represent a transformation from the origin of the preoperative image scan to the position and orientation of the combination marker.

Figure 7:
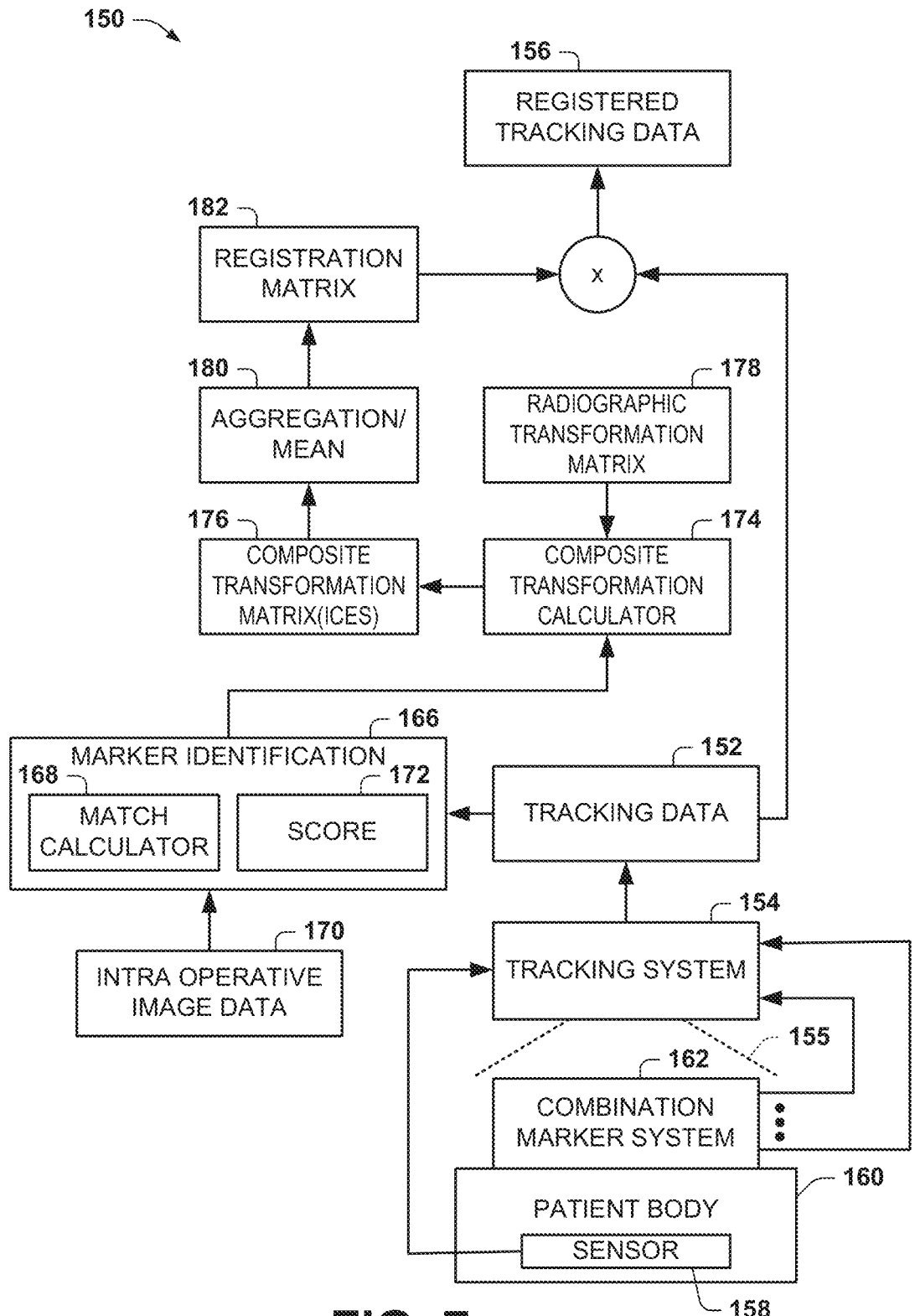
FIG. 7 depicts an example of a system that can be utilized to generate registered tracking data.

FIG. 7 depicts an example of a system 150 for translating tracking data 152 that is acquired from a tracking system 154 into corresponding registered tracking data 156, which is registered in a common coordinate system with an implicit anatomical model (e.g., as defined by model data 20 of FIG. 1). As disclosed herein, the common coordinate system can represent a coordinate system for image data that has been acquired preoperatively relative to the tracking data that is generated intraoperatively by the tracking system 154. As an example, the tracking system 154 can generate the tracking data 154 to represent a position and orientation of one or more sensors 158 being positioned within a patient's body 160.

A combination marker system 162 (e.g., one or more combination marker 104 of FIGS. 3-6) can be attached to the patient's body 160. In the example of FIG. 7, the combination marker system 162 can include one or more sensors that provide respective signals to the tracking system indicative of a location of the combination marker within the coordinate system of the tracking system 154. One or more other sensors can be affixed relative to an object that is movable within the patient's body 160 for identifying a location of such sensor in the coordinate system of the tracking system. Each such sensor 158 thus can also provide a signal to the tracking system based on which the tracking system can compute corresponding tracking data for such sensor. As mentioned, the tracking data 152 represents a position and orientation of each respective object sensor 158 as well as marker sensors within the combination marker system 162.

The tracking system 154 can provide the tracking data with an output sample rate to enable computation of real time positioning and visualization of the object to which the sensor is attached as well as the combination marker system. Since the combination marker system 162 is attached to the patient's body 160, the coordinate system of the tracking system 154, the registered tracking data 156 is consistently computed to accommodate for movement in the patient's body 160. For example, the tracking system 154 can include a transmitter (e.g., an electromagnetic field generator) that provides a non-ionizing field, demonstrated at 155, which is detected by each sensor 158 to provide a corresponding sensor signal to the tracking system. An example tracking system 154 is commercially available from Northern Digital, Inc., of Ontario, Canada. The tracking system 154 can provide the tracking data 152 at an output sample rate (e.g., sixty samples per second) for each sensor sufficient to enable substantially real time determination of sensor location (e.g., to provide a vector describing sensor position and orientation). The tracking processing subsystem thus can process each frame of tracking data such that the registered tracking data can likewise represent real time tracking data acquired by the tracking system that can be registered into the coordinate system of the anatomical model and rendered as a graphical representation, as disclosed herein.

The marker identification function 166 can be configured to identify each composite marker (e.g., the marker 104). For instance, the marker identification function 166 is programmed to associate a tracking system sensor with a respective combination marker. For example, the marker identification function 166 can include a match calculator 168 programmed to compute a distance between the respective markers in the coordinate space (e.g., electromagnetic space) of the tracking system and in the intraoperative image coordinate system, as represented by intraoperative image data 170. For example, the match calculator 168 can be programmed to compute a difference between the distance between two markers in tracking system coordinate system and in the intraoperative image coordinate system. The match calculator 168 can also compute a difference between angles between two markers Z axis in both the tracking system coordinate system and the intraoperative image coordinate system.

Based upon the computations by the match calculator, a scoring function 172 can assign a score to represent the quality and results of the matching calculation. For example, the scoring function 172 can assign a score to each combination marker can be the sum of scores computed based upon each calculation performed by the match calculator 168. The marker identification function 166 can in turn identify which tracking system marker corresponds to which radio opaque marker from the image operative image data 170. The results of the scoring and analysis by the marker identification function 166 can be utilized to generate a corresponding tracking system transformation.

A composite transformation calculator 174 can compute a corresponding composite transformation matrix for each combination marker in the combination marker system 162. As mentioned, the combination marker system can include one or more composite markers each of which can result in a corresponding composite transformation matrix 176. The composite transformation calculator 174 can compute the composite transformation matrix 176 based upon the pre-computed radiographic transformation matrix 178 (e.g., corresponding to the radiographic transformation matrix 102 of FIG. 3) and the tracking system transformation information provided by the marker identification function 166. For example, the calculator 174 can multiply the tracking system transformation information by the inverse of the radiographic transformation matrix 178 to generate the corresponding composite transformation matrix from the coordinate system of the tracking system 154 to the coordinate system in which the anatomical model resides.

As disclosed herein, in some examples the coordinate system of the anatomical model can correspond to the coordinate system of the preoperative image data. In examples where multiple combination markers are utilized in the combination marker system 162, a corresponding composite transformation matrix can be computed for each combination marker. An aggregation function 180 can in turn compute a corresponding registration matrix 182 such as corresponding to the mean or average of the all combination marker composite transformation matrixes 176. The corresponding tracking data for a given frame for which the registration matrix 182 has been computed can in turn be multiplied by the registration matrix 182 to provide the corresponding registered tracking data for the given frame of such tracking data. As mentioned, a corresponding registration matrix 182 can be computed for each frame of tracking data such that the registered tracking data can be generated on a frame by frame basis, such as for tracking data acquired over one or more sequences of frames.

Figure 8:
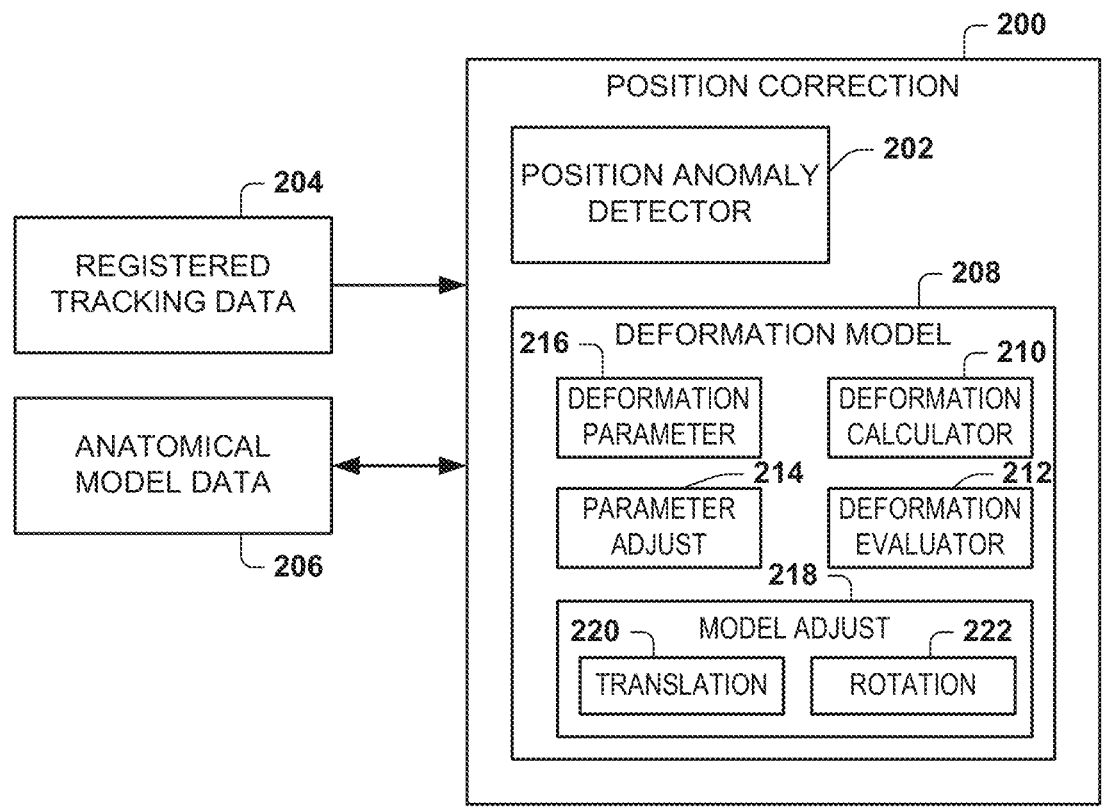
FIG. 8 depicts an example of a position correction system that can be utilized to correct a position of an implicit model for a visualization.

FIG. 8 depicts an example of position correction function 200 that can be implemented (e.g., by output generator 26 of FIG. 1 or output generator of FIG. 14) to correct a position of the anatomical structure represented by the implicit anatomical model (e.g., based on corresponding to anatomical model data 20 of FIG. 1). The position correction function 200 can be programmed to implement deformation corrections that can occur in response to insertion of an object (e.g., an instrument such as a catheter or guide wire) into an elongated anatomical structure such as a patient's vasculature. As just described with respect to FIG. 7, the position of sensors attached to an intravascular instrument can be constantly monitored and updated as part of the real time registered tracking data.

As the instrument or other object is moved within anatomical region of interest, the anatomical structure may deform and such deformation can be identified and utilized to modify the anatomical model data that is utilized to generate a visualization of the anatomic structure. For example, the position correction function 200 can include a position anomaly detector 202 that is programmed to detect a condition when an adjustment to the anatomical model is necessary to provide a visually accurately representation of the instrument within the anatomical structure. The position correction function 200 thus can employ a deformation evaluator 212 to analyze the registered tracking data for the instrument relative to the anatomical model data to determine whether or not a deformation condition exists that requires correction.

For example, the registered tracking data 204 can be utilized to construct a visualization of an instrument or other object carrying one or more sensors (e.g., sensors 158 detectable by tracking system 154 of FIG. 7) that are moving within the anatomic structure of the patient's body. In this example, the anatomical model data 206 can correspond to a fixed representation of the patient's anatomic structure that can be adjusted spatially according to a deformation parameter 216 of a deformation model 208. Thus, by adjusting the deformation parameter a desired amount of deformation can be imposed on the model such that the object resides within the patient's anatomic structure, a resulting output visualization.

By way of example, the position anomaly detector 202 can detect if the deformation evaluator determines that the object represented by the tracking data 204 is outside a volume of the anatomic structure provided by the anatomical model data 206. If the position of the object represented by the tracking data resides within the volume, the position anomaly detector can determine that the vessel is not deforming such that the anatomical model data 206 can remain unchanged by the position correction function 200. If the position anomaly detector 202 determines that the object represented by the registered tracking data 204 is outside the volume of the anatomical structure represented by the anatomical model data 206 the position anomaly detector can instruct the deformation model 208 that the anatomical structure is deforming.

The deformation model 208 can include one or more parameters 216 that can be modified by a parameter adjust function 214 to adapt the shape of the elongated anatomical structure based on a corresponding amount of deformation that is determined. The deformation model 208 can include a deformation calculator 210 that is programmed to determine compute positions of the object and the boundary (e.g., surface) of the anatomical structure. A deformation evaluator 212 can compare the computed positions and determine if the computed position information indicates that the object represented by the registered tracking data is outside the structure represented by the anatomical model. In response to the deformation evaluator 212 determining that deformation exists, the parameter adjust function 214 can adjust the deformation parameter 216. The deformation parameter 216 can be applied to the anatomical model data to implement a corresponding adjustment to the anatomical model 206. For example, a model adjustment function 218 can include a translation component 220 and a rotation component 222 for adjusting different components of the anatomical model according to a value of the deformation parameter.

Figure 9:
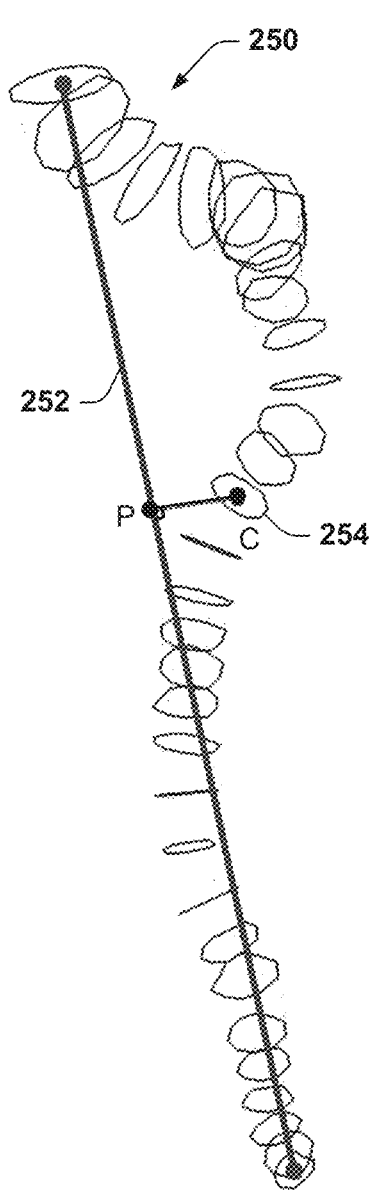
FIG. 9 depicts an example of a visualization of an anatomical structure demonstrating translational correction that can be implemented with respect to an implicit model.
Figure 10:
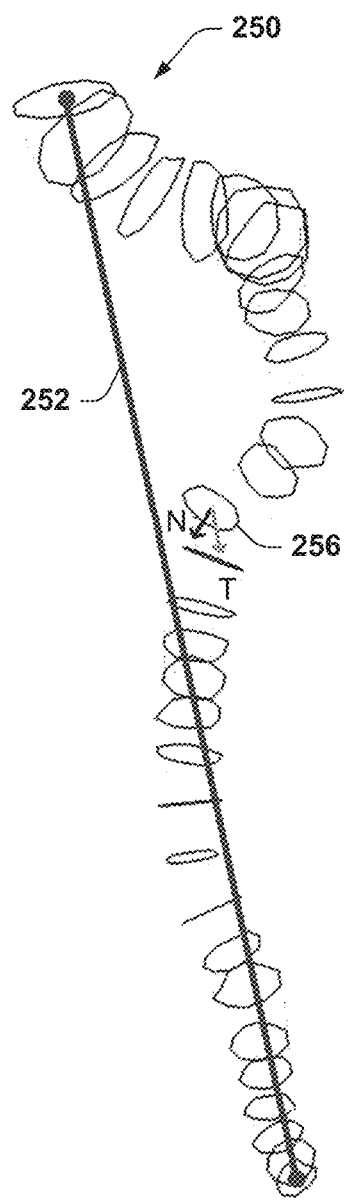
FIG. 10 depicts an example of a visualization of an anatomical structure demonstrating rotational correction that can be implemented with respect to an implicit model.
Figure 11:
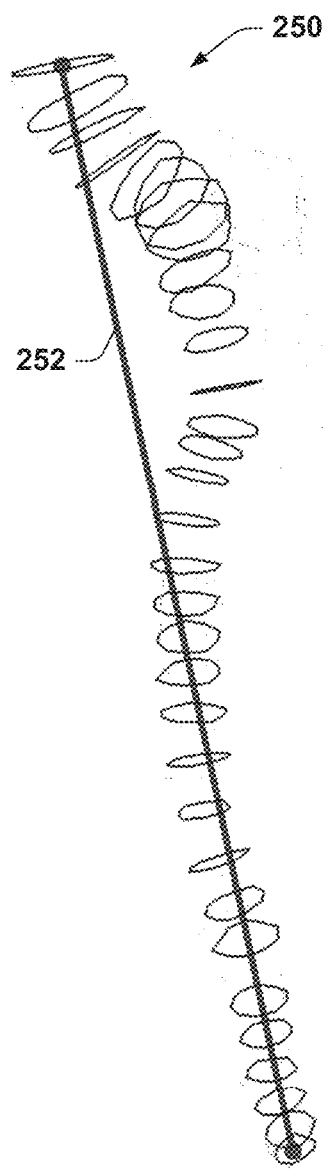
FIG. 11 depicts an example of visualizations of an anatomical structure demonstrating both translation and rotation implemented with respect to an implicit model.

By way of example, FIGS. 9, 10 and 11 demonstrate operations that can be performed by the model adjustment function 218 to implement deformation of an implicit model, which is demonstrated as a vessel model 250. While the examples of FIGS. 9-11 are described in the context of a vessel model 250, other types of anatomical structures could be deformed in a similar manner. In the example of FIGS. 9-11, the deformation can be implemented by perturbing the vessel model to more closely follow a straight path corresponding to an elongated instrument. As demonstrated in FIGS. 9-11, the straight path can be defined by an axis 252, such as a straight line segment whose endpoints are the centroids of the first and last slices of the vessel model 250. Other shapes of paths, such as a curved path or a computed shape of the object could also be utilized as the goal towards which the model 250 is deformed.

For the example where the implicit model is a lofted b-spline, the model adjust function 218 can perform the deformation operation on the geometric knots which define each cross-sectional slice of the implicit model. As discussed with respect to FIG. 2, when the implicit model is computed, the knots correspond to the actual geometry of the surface derived from the image data. By transforming these knots, the model adjustment function 218 of the correction method 200 can adjust the shape of the vessel model 250. For any given slice, all knots are transformed together to retain the correct cross-sectional shape, and each slice can undergo both translation and rotation.

FIG. 9 demonstrates an example of how translation can be computed (e.g., by translation function 220) for a given slice 254. The translation function 220 can compute the slice's centroid C. The translation function 220 can also compute a point P on the axis 252 that is nearest C. The translation function 220 can compute a vector CP which is multiplied by the deformation parameter 216. This vector is then added to each geometric knot in the slice. The effect is that slice is translated along the vector from C to P by an amount commensurate with the computed deformation parameter 216.

With reference to FIGS. 8 and 10, the rotational adjustment function 222 is programmed to compute a rotational deformation for each slice in the model 250 based on the deformation parameter 216. The rotational adjustment function 222 can rotate the slice 256 so that its plane lies more perpendicularly to the axis 252, with the relative perpendicularity depending on (e.g., being proportional to) the deformation parameter 216. The rotational adjustment function 222 can compute a unit normal vector N that is perpendicular to the plane of the slice 256. The rotational adjustment function 222 can also compute unit vector T parallel to the axis 252 and extending through the centroid of such slice.

The rotational adjustment function 222 can compute a cross product N×T and the direction of the cross product yields an axis of rotation. The rotational adjustment function 222 can compute the arc-cosine of the magnitude of the cross product to determine an angle of rotation. If each point on the slice were rotated about this axis by this angle, the slice would become perpendicular to the axis. For each slice in the model 250, the rotational adjustment function 222 thus is programmed to multiply the computed angle of rotation by the deformation parameter 216 and then perform the rotation as a fractional part of the computed angle of rotation based on deformation parameter. FIG. 11 demonstrates an example of the vessel model 250 after both translation and rotation have been performed on the model.

Figure 12:
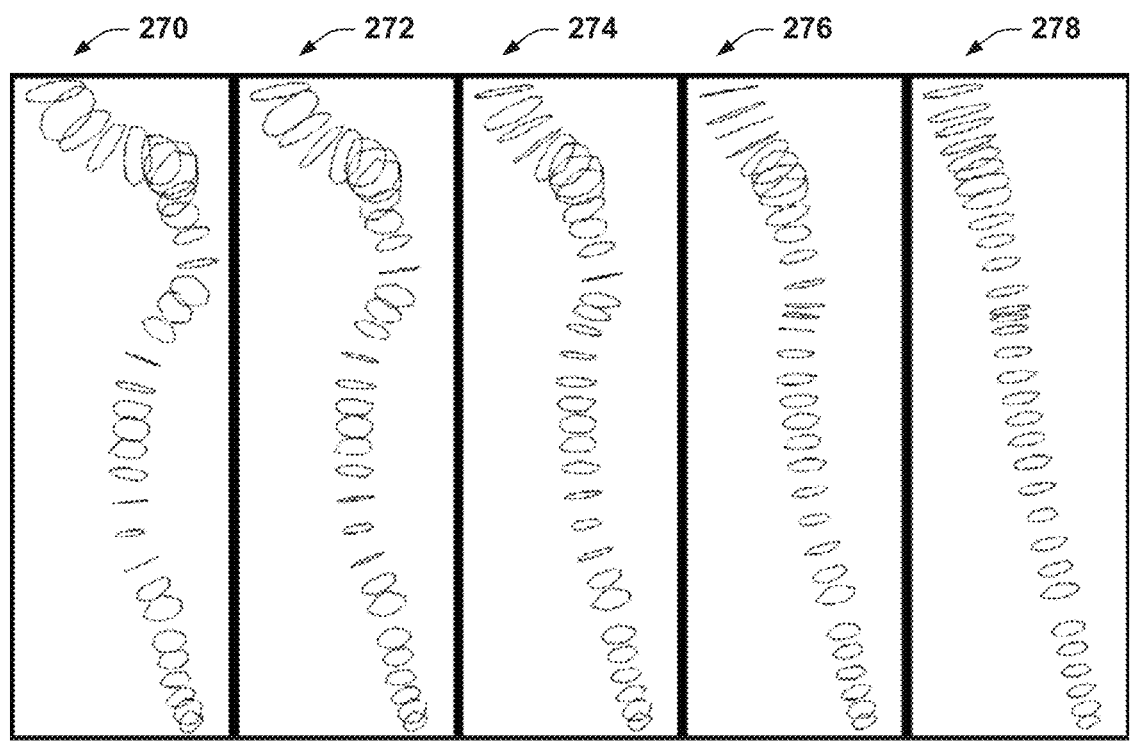
FIG. 12 depicts an example of visualizations of an anatomical structure based on an implicit model with different levels of correction.
Figure 13:
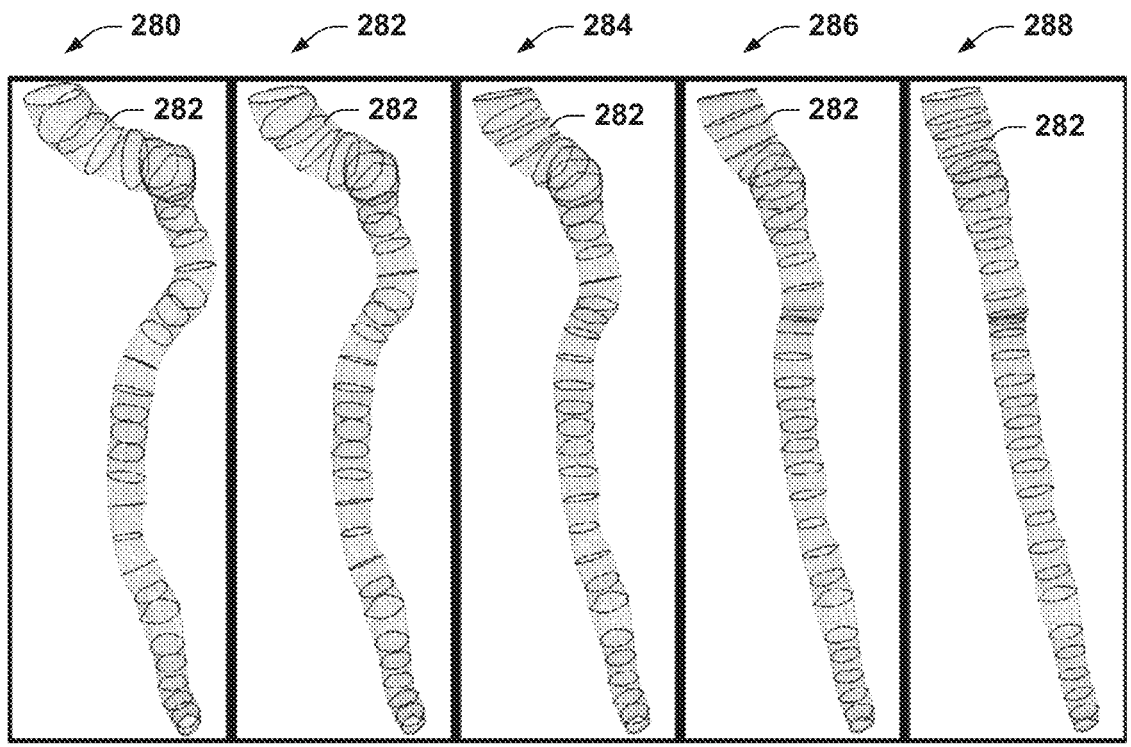
FIG. 13 depicts an example of visualizations of an anatomical structure including a surface rendering based on an implicit model with different levels of correction.

FIG. 12 depicts examples of a vessel model demonstrating different amounts of deformation, demonstrated at 270, 272, 274, 286 and 278. For instance, each example model 270, 272, 274, 286 and 278 can be generated based on applying different values of deformation parameters that have been computed (e.g., by parameter adjust function 214), such as disclosed herein. FIG. 13 demonstrates vessel models 280, 282, 284, 286, and 288 computed for different deformation parameter and including a surface 290 that has been rendered for each respective model such as by connecting each respective slice, such as by connecting each slice with a cylindrical segment.

Figure 14:
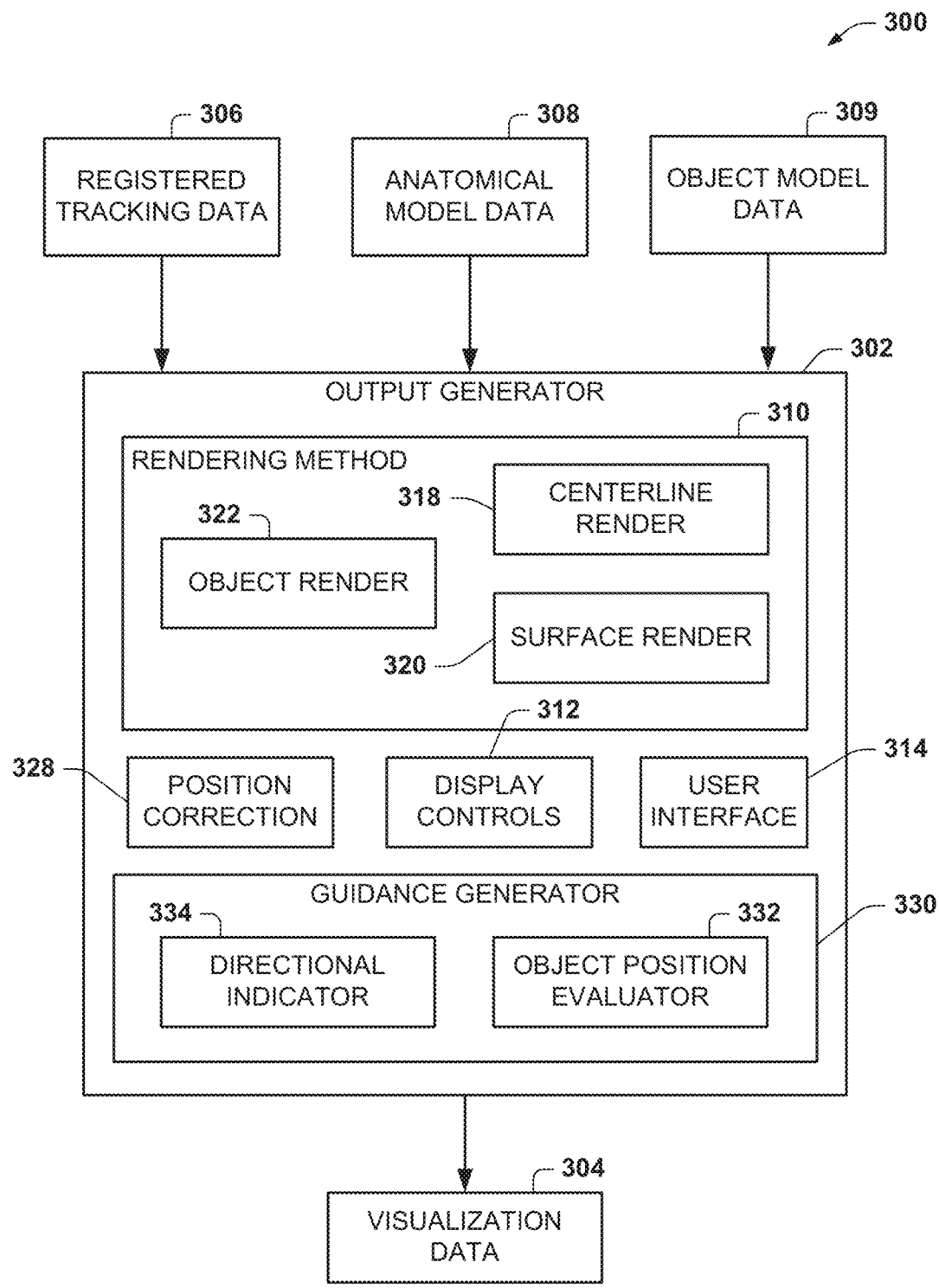
FIG. 14 depicts an example of an output generator that can be implemented for generating an output visualization.

FIG. 14 depicts an example of a visualization system 300 that includes an output generator 302 programmed to generate visualization data 304, which can be provided to a display to render a corresponding graphical representation. The output generator 302 can generate the visualization data 304 based on registered tracking data 306, anatomical model data 308 and object model data 309. The registered tracking data 306 can correspond to the registered tracking data 14 of FIG. 1 as well as the registered tracking data 156 of FIG. 7. The anatomical model data 308 can correspond to the anatomical model data 20 of FIG. 1 as well as the anatomical model data 54 of FIG. 2. The object model data 309 can correspond to another implicit model that has been generated as corresponding to the object. As disclosed herein, one or more sensors can be affixed to the object to enable tracking of its location by a tracking system, such as tracking system 154 of FIG. 7 that generates the tracking data from which the registered tracking data 306 is computed.

By way of example, the object model data 309 can correspond to an analytical or parametric representation of a surgical instrument, which may be a generally rigid surgical instrument or an articulated instrument that includes a flexible tip such as wires, catheters and the like. Accordingly the complexity of the model data 309 and the corresponding implicit model that it defines can vary according to the type of instrument or other object that is being tracked within the patient's anatomy. In addition to parameterizing the geometry of the object, the object model data 309 can also be configured to model other properties of the object (e.g., resilience and/or ductility).

The output generator 302 includes a rendering method 310 programmed to produce a three-dimensional plot corresponding to the visualization data 304 based on the input data 306, 308 and 309. Various types of rendering software (e.g., commercially available or proprietary) can be utilized and implemented as the rendering method 310 and can vary according to the type of models generated for use by the output system 300.

The output generator 302 can also include display controls 312 that can control the output that is provided intraoperatively. The display controls 312 can be configured to selectively generate any number of one or more displays concurrently on one or more screens, each of which can include a different view of the object and the anatomic structure. The respective views can be selected automatically such as by default parameters or it can be adjusted in response to the user input just as can be provided a user interface 314. This display controls 312 can further control a viewing angle for each of the visualizations of the anatomical model and the object that are presented to the user. Since the structures in each visualization are virtual renderings based on implicit models, the output visualization is not constrained to any particular viewing angle or type of visualization.

In some examples, the display controls 312 can compute and display task-specific visualizations, such as may include an optimal view for a particular task (for example, cannulating a renal artery). For example, when cannulating a vessel, it is useful to visualize the vessel and wire without distractions or obstructions. The output generator is able to create this visualization since each vessel and each device are virtual renderings. Additionally, because each the models 308 and 309 are easily separated into its constituent parts, other items can be effectively removed from the display and only show the clinician the pertinent geometry and telemetry for the task at hand. Thus, the display controls can request the rendering method 310 to produce nearly any visualization in two- or three-dimensional space, which can be rendered rapidly.

The output generator 302 can also include a position correction function 328 such as corresponding to the position correction function 200 disclosed with respect to FIG. 8. Thus, the anatomical model data 308 that is utilized by the rendering method 310 can operate on a position-corrected version of the anatomical model data that includes a corresponding deformation model for adjusting the position (e.g., translational and rotational position) of the model according to a computed deformation parameter.

In the example of FIG. 14, the rendering method 310 includes a centerline render 318 programmed to plot a centerline of the anatomic structure based on the anatomical model 308 which includes parameters to define the geometry of the anatomical structure (e.g., an elongated tubular structure such as a vessel or intestine). For example, the anatomical model data 308 can be stored as a spline curve corresponding to a series of geometric knots. The centerline render 318 can evaluate the curve by calculating spline control points from the geometric knots. The centerline render 318 can in turn evaluate the spline equation using the computed control points for a given parameter value such that the centerline is a function of a single parameter.

As an example, the centerline render function 318 can compute the centerline as a function of a single parameter (u) that goes from zero to one and varies along a path corresponding to the axis of the tubular structure taken by selecting a spacing of the parameter u. The value can be computed at each respective spacing and the rendering method 310 can plot the curve as a series of corresponding line segments drawn between the values of the parameter u. For example, if a spacing of 0.1 is selected, the curve corresponding to the centerline can be evaluated at u=0, u=0.1, u=0.2, etc. and the corresponding points for each value of u can be connected to provide a plot corresponding to the centerline of the anatomical model.

The rendering method 310 can also include a surface render function 320 that can produce a plot for a surface of the anatomical structure based on the implicit model defined by the model data 308. As an example, the surface render function 320 can compute the surface as a function of two variables, such as the variable u, which extends along the axis of the tubular structure and another parameter (v) which varies as one travels tangentially around the surface. As disclosed herein, the anatomical model data 308 can store the surface information as a series of slices in which each slice can be represented by a series of geometric knots of an elongated tubular structure.

As a further example, the surface render function 320 can compute a location of a surface point for any given (u, v) parameter tuple as follows. Each slice of the spline can be evaluated a given v parameter using the same technique as for the centerline. The result can be a series of points all on the same tangential location of the surface. Such points serve as a series of geometric knots for a new one-dimensional spline, which can then be evaluated at the given u parameter. The surface render function 320 can visualize the surface by evaluating the parameters to generate triangles that tessellate the surface. Such triangles can be rendered efficiently with various computer graphics, hardware and software. The surface render function 320, for example, can employ two spacings Su and Sv which corresponds to one spacing in the u direction and one in the v direction, respectively. For example, the surface render function 320 can iterate of over the surface, plotting triangles such as follows:

for u=0 to 1 in steps of Su
        for v=0 to 1 in steps of Sv
            point1=surface(u,v)
            point2=surface(u+Su,v)
            point3=surface(u+Su,v+Sv)
            point4=surface(u,v+sV)
            plot triangle (point1,point2,point3)
            plot triangle (point3,point4,point1)

While triangles are demonstrated above, other polygonal shapes could be used.

The rendering method 310 can also include an object render function 322 to render a graphical representation of the object based on the object model data 309 and the registered tracking data 306. As disclosed herein, there can be one or more different objects that can be rendered concurrently with respect to the patient geometry, and each object has its own model provided by the model data 309. The registered tracking data 306 represents a point of one or more sensors in three-dimensional space corresponding to the same coordinate system in which the anatomical model has been registered. The object render function 322 thus can be programmed to generate a graphical representation for each object depending on the location of the object defined by the registered tracking data.

By way of example, the object render function 322 can plot rigid objects (and parts of objects that are rigid) by applying their transformation matrix multiplied by the overall registration matrix. For the case of articulated objects (e.g., instruments with a flexible tip, such as wires and catheters), the object render function can be programmed to plot different parts of the structure separately.

Figure 15:
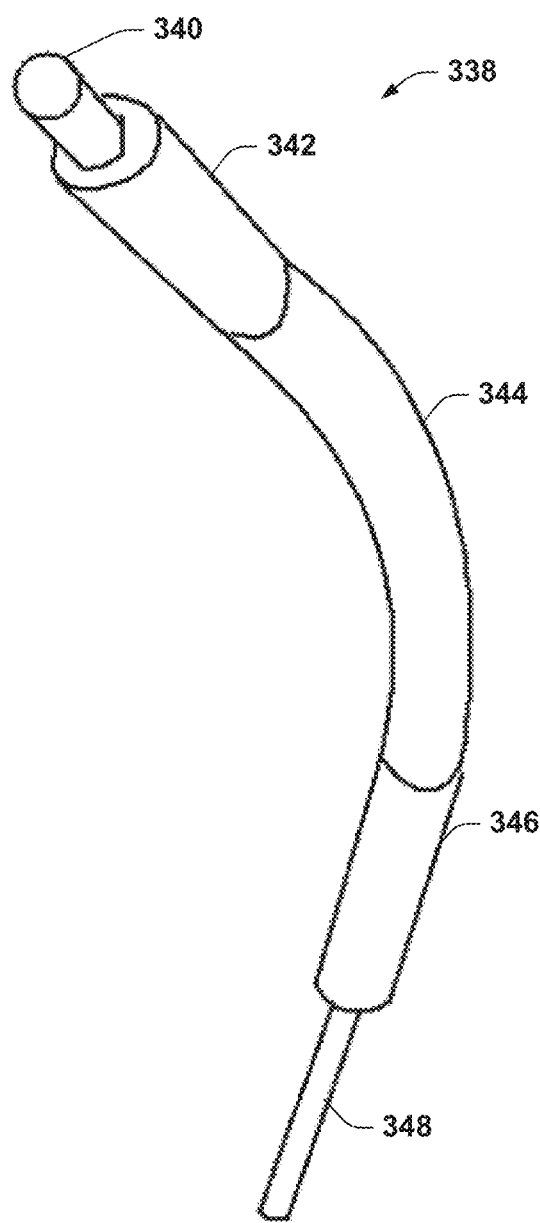
FIG. 15 depicts an example of a rendering of an elongated instrument.

As an example, the object render function 322 can render an elongated instrument in discrete parts. FIG. 15 depicts an example of a rendering of an elongated instrument (e.g., a catheter) 338 that can be generated by object render function 322 based on tracking data provided for multiple object sensors. In the example of FIG. 15, the rendering of the instrument 338 includes a tip portion 340, a distal body portion 342, a connection portion 344, a proximal body portion 346, a tail portion 348. The rending 338 of such discrete portions, based on tracking data for two or more sensors can thus represent the shape of the instrument. For example, one sensor can be affixed to an instrument in its distal body and another sensor can be affixed to the instrument in its proximal body.

As a further example, the object render function 322 can render the tip 340 as a rigid cylinder translated along the +Z axis of the distal sensor such that it resides just distal of the distal body. The distal body 342 can be rendered as a rigid cylinder at the location of the distal sensor (e.g., based on tracking data for such sensor). The object render function 322 can also render the proximal body 346 as a rigid cylinder at the location of the proximal sensor (e.g., based on tracking data for such sensor). The connection 344 can be rendered as two circles (e.g., one at the proximal tip of the distal body and one at the distal tip of the proximal body), which can be lofted by interpolating between the respective circles, such as by lofting with Bezier curves. The object render function 322 can render the tail as a rigid cylinder translated along the –Z axis of the proximal sensor such that it resides just proximal of the proximal body. The lengths, radii, and colors of each part can be selected according to the objects actual physical appearance. In some situations, non-cylindrical shapes could also be used by the object render, such as when appropriate to further match the geometry of the object being rendered.

The output generator 302 can also include a guidance generator 330 programmed to generate user perceptible guidance that can be based on the registered tracking data 306, corresponding to the location of the object, and the patient's anatomy. Some guidance can be static whereas other guidance can be dynamic. For example, the guidance generator 330 can include an object position evaluator 332 that is programmed to evaluate the position of the object based upon the registered tracking data 306 relative to the position of one or more anatomical feature that can be specified in or determined from the anatomical model data 308. Such features, for example can include bifurcations in a tubular structure or other anatomical landmarks (e.g., a target anatomical site). The guidance provided relative to such anatomical features can include a position of the feature or trajectory path along which an object may be advanced to arrive at such position.

As an example, the object position evaluator 332 thus can compute a distance between a selected feature and a point along the object (e.g., corresponding to a distal tip of an instrument or other predetermined location along the object). The object position evaluator 332 can utilize the distance to ascertain the relative proximity between the object and the anatomical feature of interest. Based upon the evaluation, the guidance generator 330 can provide a visual indicator, an audible indicator or a combination of audible and visual indicators. For example, an audible indicator can provide a series of beeps or tones that increase in frequency as a function of decreasing distance between the object and the location of the target feature. The guidance generator 330 can specify a color code to be applied to a selected feature of the output visualization, such as green to indicate that the position is on target, yellow to indicate a deviation within a predetermined parameter or red to indicate that the position is outside of expected parameters.

As a further example, the guidance generator 330 can also include a directional indicator 334 that can produce virtualized graphical indictor showing a direction that a distal tip of the object (e.g., a catheter or wire) is oriented. The graphical indicator can be rendered as a series of short lines translated along a given sensors positive Z axis. The visual indicator thus can provide an easy way to determine whether the object is aligned with a given part of the anatomical structure to facilitate advancing the object through or into a target branch vessel. The appearance of the guidance further will vary depending on the particular viewing angle that is being produced.

The guidance generated at 330 can also provide information to graphically differentiate anatomical locations or other target sites, such as by using different color codes for different structures of interest. For example, the guidance generated at 330 can render a perimeter of the ostium of each branch vessel as a thick annular line that appears surrounding the entrance to a corresponding branch. Those skilled in the art will understand and appreciate for the guidance generator 330 can provide additional feedback to the user. For example, when the tip of the object gets within a predetermined distance of an ostium, which has been indicated by a graphically differentiated ring at the branch, the ring can change colors as the tip gets within a predetermined distance.

FIGS. 16-19 depict examples of visualizations that can be generated by the output generator 302 (also corresponding to output generator 26 of FIG. 1). While the examples of FIGS. 16-19 are demonstrated in the context of a major blood vessel, namely the descending aorta, the systems and methods disclosed herein are equally applicable to generate visualizations for other anatomical structures and objects that can be positioned in the body relative to such structures.

Figure 16:
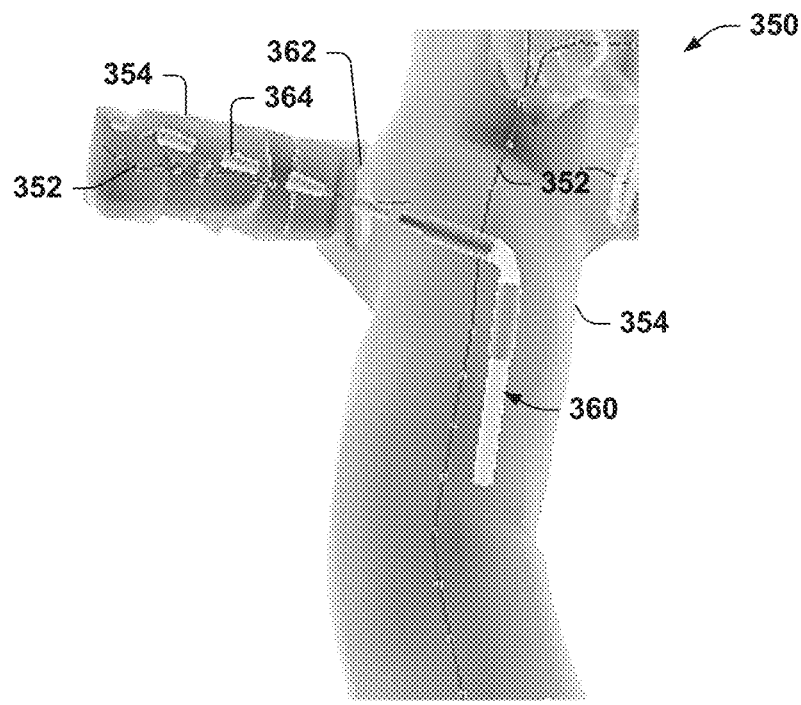
FIG. 16 depicts an example of part of an output visualization of a tracked object relative to a visualization of patient anatomy generated based on an implicit model.

FIG. 16 demonstrates a virtualized output visualization 350 that can be generated by an output generator. The visualization 350 includes a centerline 352 and a surface 354 of the vessel that can be rendered based on an implicit anatomical model of patient geometry as disclosed therein. The visualization 350 also can include a branch extending laterally from the main branch. In the example of FIG. 16, the object is demonstrated as a rendering of flexible catheter 360 having a tip that is approaching an ostium 362. As demonstrated in FIG. 16, the shape of the catheter 360 substantially matches the shape of the physical tool since the shape in the virtual rendering is provided (e.g., by object render function 322 of FIG. 14) based on tracking data generated for two or more sensors disposed on the physical tool. The visualization of FIG. 16 also illustrates an axial guidance feature 364 extending from the tip of the catheter, such as can be rendered (e.g., by guidance generator 330 of FIG. 14) as projecting outwardly from the Z axis of the object. As shown, the axial guidance feature 364 demonstrates the tip is heading in a correct direction for insertion through the ostium 362 of the adjacent branch.

Figure 17:
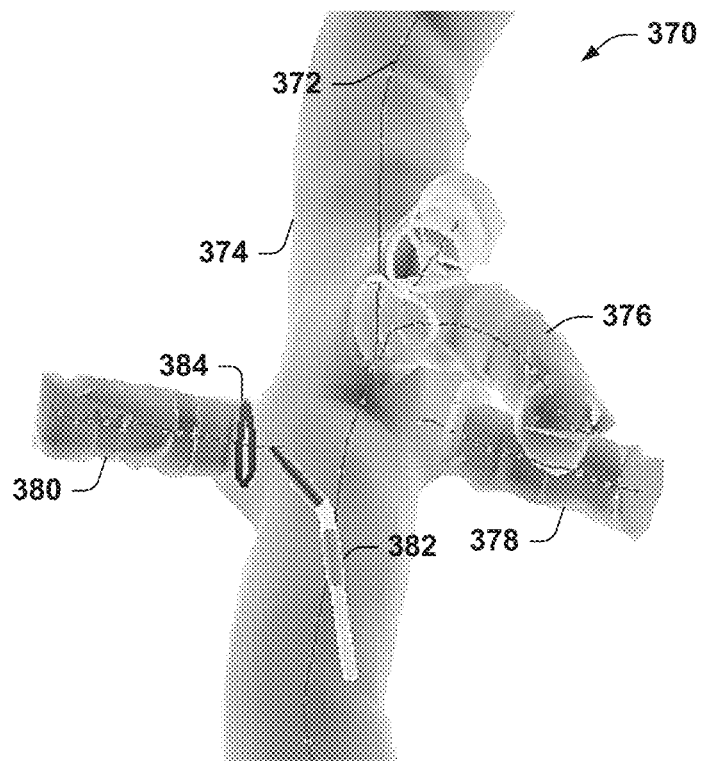
FIG. 17 depicts another example of an output visualization of a tracked object relative to a visualization of patient anatomy generated based on an implicit model . . . .

FIG. 17 demonstrates another example of an output visualization of a vessel 370 that includes a centerline 372 and surface 374 that can be rendered from an anatomical model data. The example of FIG. 17 demonstrates a plurality of branches 376, 378 and 380 that extend outwardly from the main branch. A flexible elongated object, such as a catheter (or other instrument) 382 is also rendered in the visualization based on registered tracking data and a corresponding object model. The catheter 382 is demonstrated as advancing towards an ostium 384 of the branch 380, and the ostium changes color providing guidance that the catheter is on target, for example.

Figure 18:
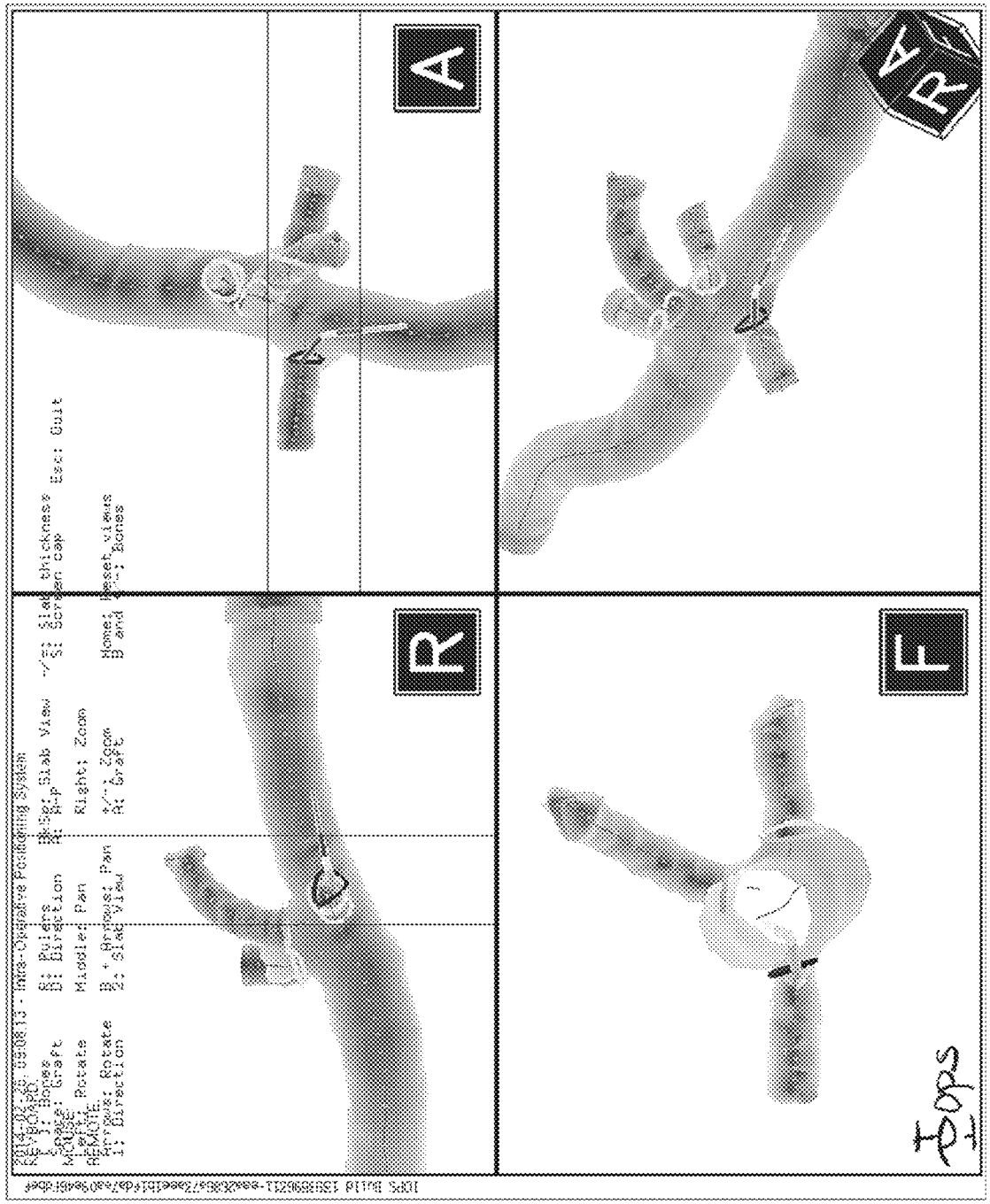
FIG. 18 depicts an example of a plurality of concurrently generated output visualizations that can be generated concurrently for a plurality of different views.
Figure 19:
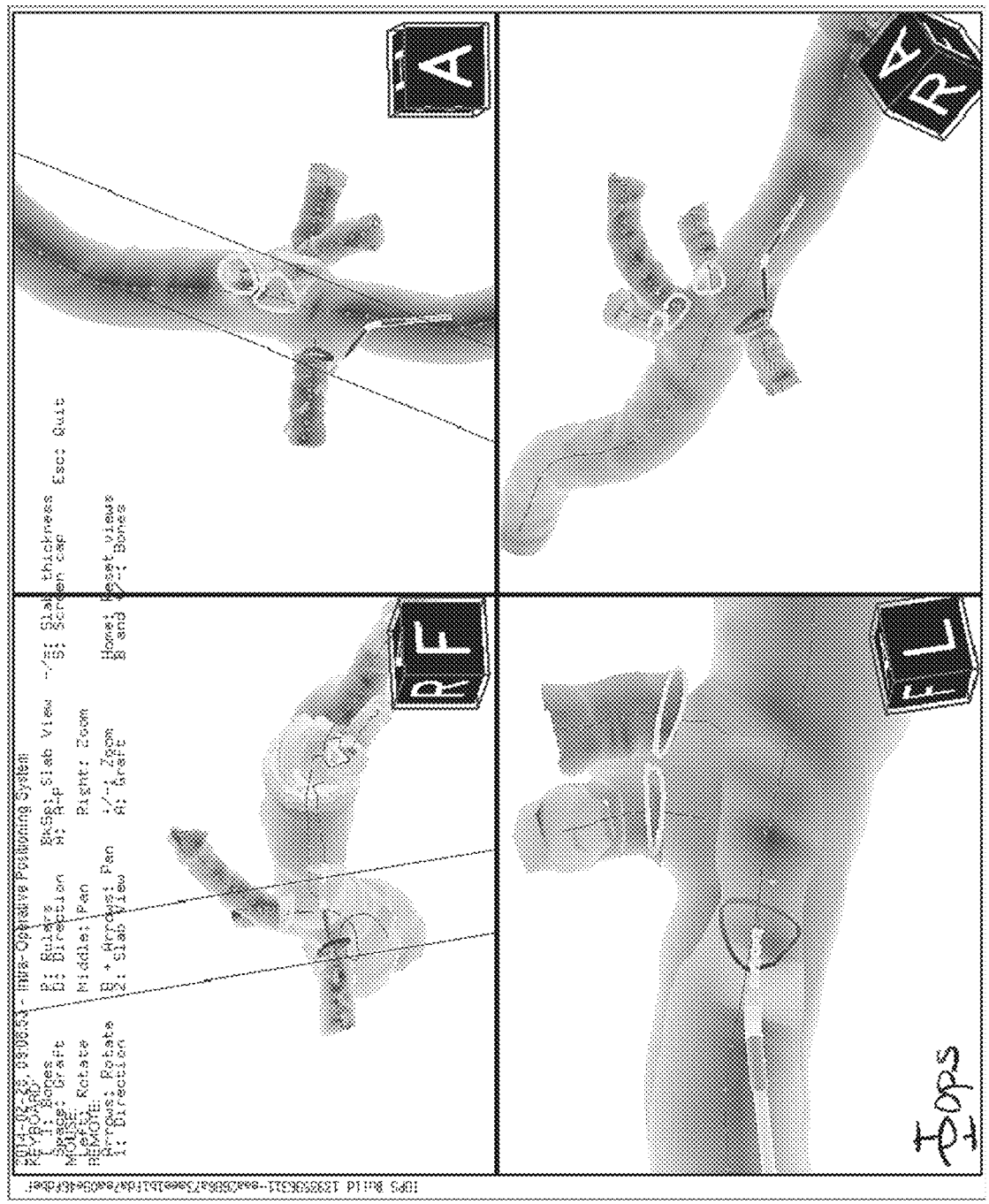
FIG. 19 depicts an example of another output visualization demonstrating a plurality of output visualizations that can be generated concurrently for different views angles.

FIG. 18 demonstrates an output visualization 400 that includes a plurality of different windows from different orthogonal views in a corresponding coordinate system. In each of the view in the example of FIG. 18, the patient anatomy and object is generated concurrently based on anatomical model data and based on a corresponding sample or frame of registered tracking data. As disclosed herein, each of the views can be user selectable views in response to a user input. The size of views and the information presented can be varied automatically and/or in response to user input. FIG. 19 depicts an example of another set of output visualizations that can be generated in a multiport format concurrently based upon anatomical model data and registered tracking data.

Figure 20:
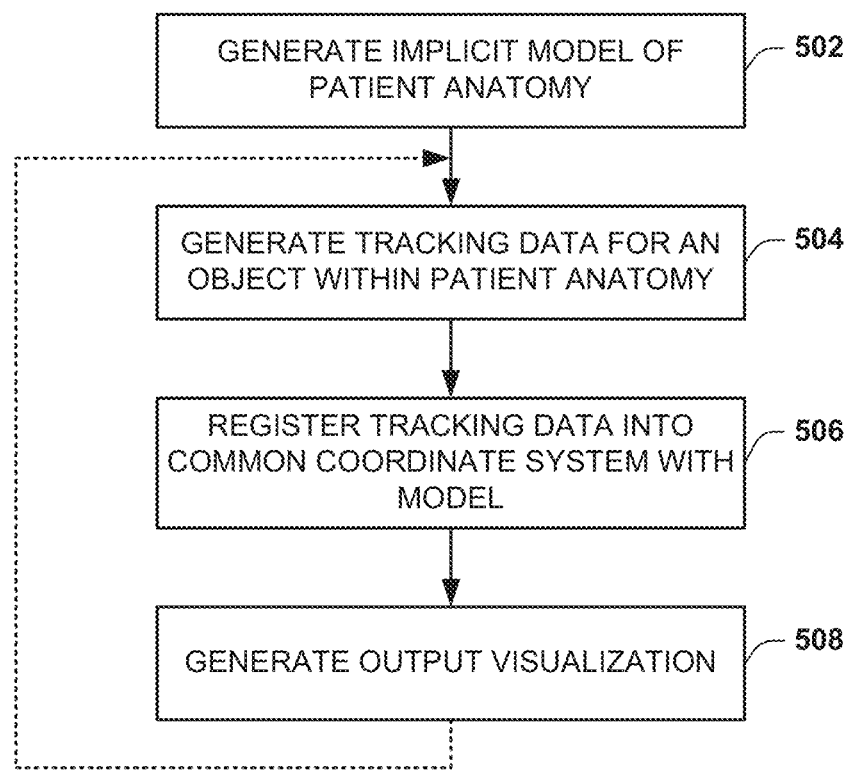
FIG. 20 is a flow diagram depicting an example of a method that can be implemented to facilitate intraoperative positioning.

In view of the foregoing structural and functional features described above, methods that can be implemented will be better appreciated with reference to FIG. 20. While, for purposes of simplicity of explanation, the method of FIG. 20 is shown and described as executing serially, it is to be understood and appreciated that the present invention is not limited by the illustrated order, as some aspects could, in accordance with the present invention, occur in different orders and/or concurrently with other aspects from that shown and described herein. Moreover, not all illustrated features may be required to implement a method in accordance with an aspect of the present invention. The methods or portions thereof can be implemented as instructions stored in a non-transitory storage medium as well as be executed by a processor of a computer device or special purpose computer device (e.g., a dedicated computer or workstation) to access data sources and perform the functions disclosed herein, for example.

FIG. 19 depicts an example of a method 500 that can be implemented to facilitate intraoperative positioning and guidance. At 502 an implicit model for the geometry of a patient's anatomy can be generated (e.g., by model generator 52 of FIG. 2) based on image data as disclosed herein. The anatomical model and corresponding image data can be stored in memory.

At 504, tracking data can be generated (e.g., by tracking system 154 of FIG. 7) to provide an indication of location for an object. The tracking data can be stored in memory for processing. As disclosed herein, the object can be an instrument or other device that is moveable intraoperatively within a patient. For example, the tracking data can be generated in response to signals provided by one or more sensors carried on the object that is being positioned intraoperatively in the patient (e.g., transluminally or endovascularly). As disclosed herein, the tracking data can be generated for the object in the absence of ionizing radiation, which is in contrast to conventional x-ray fluoroscopy.

At 506, the tracking data and the patient implicit specific model can be registered (e.g., by registration engine 12 of FIG. 1) in a common three-dimensional coordinate system. For example, the coordinate system can be the coordinate system of the preoperative image based on which the implicit model for the anatomical structure of the patient has been generated.

At 508, an output visualization can be generated (e.g., by output generator 26 of FIG. 1 or generator 302 of FIG. 14) to represent a location of the object relative to the geometry of the anatomical structure. For example, the output visualization can represent a position, orientation and shape of the object in three-dimensional space based on multi-sensor tracking data that has been registered into a common coordinate system with the implicit anatomical model (e.g., corresponding to a preoperative image space). The generating tracking data, registration of the tracking data and implicit model and generating of the output visualization can be repeated over time in response to tracking data that is generated. In this way the output visualization can be dynamically updated (e.g., in real time), such as according to an output sample rate at which the tracking data is generated. Accordingly, the output visualization can be generated in substantially real time to facilitate positioning and guidance of the object. The output visualization can include any number of concurrently generated views, which can be modified (e.g., in response to a user input or deformation correction), such as disclosed herein.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. A method comprising:
   accessing a memory to retrieve pre-operative image data for a patient;
   generating a patient-specific implicit model based on the pre-operative image data, wherein the patient-specific implicit model includes parameters that define a geometry of an anatomical structure of the patient;
   storing the patient-specific implicit model in the memory;
   receiving tracking data from an electromagnetic tracking system representing a location of a sensor attached to an object within the patient in a tracking coordinate system of the electromagnetic tracking system, wherein the tracking data is received intraoperatively based on an output of the sensor, wherein the output comprises a sensor signal provided in response to an electromagnetic field emitted by the electromagnetic tracking system;
   storing the tracking data in the memory;
   receiving intraoperative image data for the patient, wherein the intraoperative image data comprises one or more images captured intraoperatively of the anatomical structure of the patient and at least one combination marker device positioned on the patient, the at least one combination marker device comprising an image marker detectable by an imaging modality and an other marker detectable by the electromagnetic tracking system;
   generating a radiographic transformation matrix based on an image space transformation matrix and an image-marker transformation matrix, the image space transformation matrix being generated based on the intraoperative image data and the pre-operative image data, the image-marker transformation matrix being generated based on the intraoperative image data and characterizing a location of the at least one combination marker device in an image-marker coordinate system;
   computing a registration matrix based on a tracking-marker coordinate system for the at least one combination marker device and the radiographic transformation matrix, such that the registration matrix provides a transformation from the tracking coordinate system to a common three-dimensional coordinate system;
   registering the tracking data based on the registration matrix in the common three-dimensional coordinate system in which the patient-specific implicit model is also registered; and
   generating an output visualization representing a shape of the object and a location of the object relative to the geometry of the anatomical structure of the patient in the common three-dimensional coordinate system based on the registration, the geometry of the anatomical structure including a three-dimensional surface that is rendered spatially in the output visualization in the common three-dimensional coordinate system based on the registration and computing geometry of the three-dimensional surface as a function of the parameters of the patient-specific implicit model.

2. The method of claim 1, wherein the tracking data includes a position and orientation of the object in the tracking coordinate system.

3. The method of claim 1, wherein the tracking data comprises a plurality of frames generated by the electromagnetic tracking system over time according to an output sample rate of the sensor, the tracking data for each of the plurality of frames including a position and an orientation for the object in the tracking coordinate system, the registering of the tracking data and the generating of the output visualization being repeated for each of the plurality of frames of the tracking data.

4. The method of claim 1, wherein the patient-specific implicit model comprises a lofted basis spline including parameters representing the surface and a centerline of the geometry of the anatomical structure.

5. The method of claim 1,
   wherein the anatomical structure of the patient comprises an elongated tubular structure that includes a lumen,
   wherein the parameters include surface model parameters to describe a three-dimensional geometry of a surface geometry of the elongated tubular structure along a length thereof, the surface geometry of the elongated tubular structure being rendered in the output visualization by plotting polygons to tessellate the three-dimensional geometry of the surface geometry of the elongated tubular structure as a function of as a function of the surface model parameters.

6. The method of claim 1, wherein the anatomical structure of the patient comprises a blood vessel, a part of a gastrointestinal tract, a part of a respiratory tract, or a part of a reproductive tract.

7. The method of claim 1, wherein the tracking coordinate system of the electromagnetic tracking system is different from the three-dimensional coordinate system of the patient-specific implicit model that is generated based on the pre-operative image data.

8. The method of claim 1, wherein generating the output visualization further comprises plotting polygons to tessellate the three-dimensional surface as a function of the model parameters of the patient-specific implicit model.

9. The method of claim 1, wherein the parameters of the patient-specific implicit model define a surface geometry and a centerline geometry of an anatomical lumen of the patient's body, such that the output visualization represents the location of the object relative to at least one of the surface geometry or the centerline geometry of the anatomical lumen, including during movement of the object along the anatomical lumen of the patient's body.

10. The method of claim 9, wherein the object is a catheter, the sensor located adjacent a distal end of the catheter.

11. The method of claim 1, further comprising acquiring the intraoperative image data via the imaging modality, wherein the other marker has a location that is included as part of the tracking data, the image marker and the other marker having a predetermined fixed spatial relationship with respect to each other; and
    computing the image space transformation matrix based on the predetermined fixed spatial relationship between the image marker and the other marker.

12. The method of claim 11, wherein the at least one combination marker device is a plurality of combination markers, the plurality of combination markers being disposed in a fixed spatial relationship on a marker pad device that is positioned on the patient.

13. The method of claim 11, wherein the generating the radiographic transformation matrix comprises:

computing the image-marker coordinate system for the image marker based on the intraoperative image data; and computing the image-marker transformation matrix based on the image-marker coordinate system.

14. The method of claim 13, further comprising determining the tracking-marker coordinate system for each of a plurality of combination markers based on the tracking data acquired intraoperatively.

15. The method of claim 14,
wherein the tracking data comprises a plurality of frames of the tracking data generated by the electromagnetic tracking system over time, the tracking data for each of the plurality of frames of including a position and an orientation for the object in the tracking coordinate system,
wherein determining the tracking-marker coordinate system and computing the registration matrix is repeated for each of the plurality of frames of the tracking data, such that the output visualization varies dynamically over time.

16. One or more non-transitory machine readable media having instructions programmed to perform the method of claim 1.

17. A system comprising:
an electromagnetic tracking system including at least one field generator to generate an electromagnetic field external to a patient's body and a sensor attached to an object that is moveable within an anatomical structure of the patient;
a non-transitory memory configured to store machine-readable instructions and pre-operative image data; and
a processing unit configured to access the memory and execute the machine-readable instructions to:
generate a patient-specific implicit model based on the pre-operative image data, wherein the patient-specific implicit model includes a set of one or more equations having one or more model parameters that defines a three-dimensional geometry of the anatomical structure of the patient in a three-dimensional space;
receive tracking data from the electromagnetic tracking system representing a location of the sensor within a tracking coordinate system of the electromagnetic tracking system, wherein the tracking data is provided intraoperatively based on a sensor signal provided by the sensor in response to the electromagnetic field emitted by the tracking system;
store the tracking data in the memory;
retrieve intraoperative image data for the patient, wherein the intraoperative image data comprises one or more images captured intraoperatively of the anatomical structure and at least one combination marker device positioned on the patient, the at least one combination marker device comprising an image marker detectable by an imaging modality and an other marker detectable by the electromagnetic tracking system;
generate a radiographic transformation matrix based on an image space transformation matrix and an image-marker transformation matrix, the image space transformation matrix being generated based on the intraoperative image data and the pre-operative image data, the image-marker transformation matrix being generated based on the intraoperative image data and characterizing a location of the at least one combination marker device in an image-marker coordinate system;
compute a registration matrix based on a tracking-marker coordinate system for the at least on combination marker device and the radiographic transformation matrix, such that the registration matrix provides a transformation from the tracking coordinate system to a common three-dimensional coordinate system;
apply the registration matrix to the tracking data to transform the tracking data from the tracking coordinate system of the electromagnetic tracking system to the common three-dimensional coordinate system; and
generate a three-dimensional graphical visualization representing the object at a location relative to the geometry of the anatomical structure of the patient in the common three-dimensional coordinate system based on the registration matrix, the geometry of the anatomical structure including a three-dimensional surface that is rendered spatially in the output visualization in the common three-dimensional coordinate system based on the registration matrix, the geometry of the three-dimensional surface being computed as a function of the respective model parameters of the patient-specific implicit model.

18. The system of claim 17, wherein the tracking data comprises a plurality of frames that each represent a location of the sensor at discrete times, the tracking data for each of the plurality of frames comprises a position and an orientation for the object in the tracking coordinate system, wherein the registered tracking data is generated for each of the plurality of frames.

19. The system of claim 17, wherein the registration matrix is computed by:
determining the image-marker coordinate system for each image marker within the pre-operative image data; and
computing the image-marker transformation matrix based on the image-marker coordinate system.

20. The system of claim 17, wherein the tracking coordinate system of the electromagnetic tracking system is different from the three-dimensional coordinate system of the patient-specific implicit model that is generated based on the pre-operative image data.

21. The system of claim 17, wherein the patient-specific implicit model comprises a lofted basis spline including parameters representing a surface and a centerline of the three-dimensional geometry of the anatomical structure of the patient.

22. The system of claim 21, wherein the anatomical structure of the patient comprises an elongated tubular anatomical structure that includes a lumen.

23. The system of claim 17, wherein the patient-specific implicit model defines a geometry of an anatomical lumen of the patient's body, such that the graphical visualization represents the location of the object relative to the geometry of the anatomical lumen, including during movement of the object along the anatomical lumen of the patient's body.

24. The system of claim 23, wherein the object is a catheter, the sensor located adjacent a distal end of the catheter.

25. The system of claim 17, further comprising:
an intraoperative imaging modality provide the intraoperative image data, wherein the other marker includes at least one sensor detectable by the electromagnetic tracking system and having a location that is included as part of the tracking data, the image marker and the other marker having a predetermined fixed spatial relationship with respect to each other, the radiographic transformation matrix being generated further based on the predetermined fixed spatial relationship between the image marker and the other marker.

26. The system of claim 25, wherein the at least one combination marker device is a plurality of combination markers, the plurality of combination markers being disposed in a fixed spatial relationship on a marker pad device that is positioned on the patient.

27. A system comprising:
an electromagnetic tracking system including at least one field generator to generate an electromagnetic field from a location external to a patient's body;
a sensor attached to a catheter that is moveable within an anatomical lumen of the patient, the sensor configured to communicate a sensor signal to the electromagnetic tracking system in response to the electromagnetic field;
a non-transitory memory configured to store machine-readable instructions; and
a processing unit configured to access the memory and execute the machine-readable instructions to:
store a patient-specific implicit model generated based on pre-operative image data of the patient, wherein the patient-specific implicit model describes a three-dimensional geometry of the anatomical lumen of the patient as a function of parameters for a centerline model and a surface model;
receive tracking data from the electromagnetic tracking system representing a location of the sensor attached to the catheter within the patient in a tracking coordinate system of the electromagnetic tracking system, wherein the tracking data is provided based on the sensor signal in response to the electromagnetic field intraoperatively during transluminal positioning of the catheter with respect to the anatomical lumen of the patient, the tracking data being stored in the memory;
generate a radiographic transformation matrix based on an image space transformation matrix and an image-marker transformation matrix, the image space transformation matrix being generated based on the intraoperative image data and the pre-operative image data, the image-marker transformation matrix being generated based on the intraoperative image data to characterize a location of at least one combination marker device in an image-marker coordinate system, the intraoperative image data comprising one or more images captured intraoperatively of the anatomical lumen and at least one combination marker device positioned on the patient, the at least one combination marker device comprising an image marker detectable by an imaging modality and an other marker detectable by the electromagnetic tracking system;
compute a registration matrix based on a tracking-marker coordinate system for the at least on combination marker device and the radiographic transformation matrix, such that the registration matrix provides a transformation from the tracking coordinate system to a common three-dimensional coordinate system;
register the tracking data in the common three-dimensional coordinate system based on the registration matrix in which the patient-specific implicit model is registered; and
generate an output visualization representing a shape of the catheter and a location of the catheter with respect to a visualization of the geometry of the anatomical lumen of the patient in the common three-dimensional coordinate system,
wherein the visualization of the geometry of the anatomical lumen of the patient includes a centerline and a surface that are spatially rendered in the output visualization by computing the centerline as a function of the centerline model parameter and computing the surface of the anatomical lumen as a function the centerline and the surface model parameters.

28. The system of claim 27, further comprising:
an intraoperative imaging modality to provide the intraoperative image data, wherein the other marker includes at least one sensor detectable by the electromagnetic tracking system and having a location that is included as part of the tracking data, the image marker and the other marker having a predetermined fixed spatial relationship with respect to each other.

* * * * *